(12) United States Patent
Blau

(10) Patent No.: US 12,198,330 B2
(45) Date of Patent: Jan. 14, 2025

(54) ARTIFICIAL-INTELLIGENCE-BASED DETERMINATION OF RELATIVE POSITIONS OF OBJECTS IN MEDICAL IMAGES

(71) Applicant: metamorphosis GmbH, Altenbeken (DE)

(72) Inventor: Arno Blau, Staufen (DE)

(73) Assignee: METAMORPHOSIS GMBH (DE)

( * ) Notice: Subject to any disclaimer, the term of this patent is extended or adjusted under 35 U.S.C. 154(b) by 470 days.

(21) Appl. No.: 17/309,400

(22) PCT Filed: Jun. 13, 2019

(86) PCT No.: PCT/EP2019/065618
§ 371 (c)(1),
(2) Date: May 25, 2021

(87) PCT Pub. No.: WO2020/108806
PCT Pub. Date: Jun. 4, 2020

(65) Prior Publication Data
US 2022/0058797 A1    Feb. 24, 2022

(30) Foreign Application Priority Data

Nov. 26, 2018  (LU) ........................ 101009

(51) Int. Cl.
*G06T 7/00*    (2017.01)
*A61B 6/12*    (2006.01)
(Continued)

(52) U.S. Cl.
CPC .............. *G06T 7/0012* (2013.01); *A61B 6/12* (2013.01); *A61B 6/505* (2013.01); *G06T 7/75* (2017.01);
(Continued)

(58) Field of Classification Search
CPC .................... G06T 7/0012; G06T 7/75; G06T 2207/10116; G06T 2207/30008;
(Continued)

(56) References Cited

U.S. PATENT DOCUMENTS

2009/0209851 A1    8/2009  Blau
2010/0020161 A1    1/2010  Bertrams et al.
(Continued)

FOREIGN PATENT DOCUMENTS

EP      2801320 A1    11/2014
JP   2005536236 A    12/2005
(Continued)

OTHER PUBLICATIONS

EPO, International Search Report issued in Ia PCT/EP2019/065618, mailed Aug. 14, 2019.
(Continued)

*Primary Examiner* — Marcos L Torres
(74) *Attorney, Agent, or Firm* — Lorenz & Kopf, LLP

(57) ABSTRACT

Methods and systems are described which allow a classification of first and second objects in an X-ray projection image. A respective representation and localization of both objects are determined by applying the models to match the objects in the X-ray image and a spatial relation of the classified objects is obtained. Such methods and systems take advantage of artificial intelligence.

13 Claims, 23 Drawing Sheets

(51) Int. Cl.
*A61B 6/50* (2024.01)
*G06T 7/73* (2017.01)
*G06V 20/64* (2022.01)
*G16H 30/40* (2018.01)
*G16H 50/50* (2018.01)

(52) U.S. Cl.
CPC ........... *G06V 20/647* (2022.01); *G16H 30/40* (2018.01); *G16H 50/50* (2018.01); *G06T 2207/10116* (2013.01); *G06T 2207/30008* (2013.01); *G06T 2207/30052* (2013.01); *G06V 2201/033* (2022.01)

(58) Field of Classification Search
CPC . G06T 2207/30052; G06T 2207/10121; A61B 6/12; A61B 6/505; A61B 2034/102; A61B 2034/105; A61B 2090/364; A61B 6/5211; A61B 90/00; G06V 20/647; G06V 2201/033; G16H 30/40; G16H 50/50
See application file for complete search history.

(56) References Cited

U.S. PATENT DOCUMENTS

| | | | |
|---|---|---|---|
| 2012/0071895 A1 | 3/2012 | Stahler et al. | |
| 2013/0211386 A1 | 8/2013 | Blau et al. | |
| 2014/0321710 A1 | 10/2014 | Robert et al. | |
| 2014/0343572 A1 | 11/2014 | Windolf et al. | |
| 2015/0265361 A1 | 9/2015 | Blau et al. | |
| 2018/0092619 A1* | 4/2018 | Gu | A61B 6/465 |

FOREIGN PATENT DOCUMENTS

| | | |
|---|---|---|
| JP | 2014097220 A | 5/2014 |
| JP | 2016220843 A | 12/2016 |
| JP | 2017515613 A | 6/2017 |
| WO | 2008155772 A1 | 12/2008 |
| WO | 2013106926 A1 | 7/2013 |

OTHER PUBLICATIONS

Mahfouz, M.R. et al. "A robust method for registration of three-dimensional knee implant models to two-dimensional fluoroscopy images", IEEE Transactions on Medical Imaging, Dec. 1, 2003, pp. 1561-1574, vol. 22, No. 12, IEEE Service Center, Piscataway, NJ, US, XP011103806.

Chen, X., et al. "Automatic Inference and Measurement of 3D Carpal Bone Kinematics From Single View Fluoroscopic Sequences", IEEE Transactions on Medical Imaging, Feb. 2013, pp. 317-328, vol. 32, No. 2, IEEE Service Center, Piscataway, NJ, US, XP011491223.

Ito, K. et al., "Direct assessment of 3D foot bone kinematics using biplanar X-ray fluoroscopy and an automatic model registration method", Journal of Foot and Ankle Research, Jun. 10, 2015, pp. 1-10, vol. 8, No. 21, XP055582157.

Al, J-Y, et al. "A new registration method for three-dimensional knee nearthrosis model using two X-ray images", Computer Methods in Biomechanics and Biomedical Engineering, Apr. 1, 2010, pp. 265-278, vol. 13, No. 2, XP055582413.

Yaniv, Z., et al. "Precise Robot-Assisted Guide Positioning for Distal Locking of Intramedullary Nails", IEEE Transactions on Medical Imaging, May 2005, pp. 624-635, vol. 24, No. 5, IEEE Service Center, Piscataway, NJ, US, XP011131263.

XP026906211, Prins A H et al. "Detecting femur-insert collisions to improve precision of fluoroscopic knee arthoplasty analysis", Journal of Biomechanics, Pergamon Press, New York, NY, vol. 43, vol. 3 (Mar. 3, 2010) pp. 694-700.

* cited by examiner

ARTIFICIAL-INTELLIGENCE-BASED DETERMINATION OF RELATIVE POSITIONS OF OBJECTS IN MEDICAL IMAGES

CROSS-REFERENCE TO RELATED APPLICATIONS

This application is a U.S. National-Stage entry under 35 U.S.C. § 371 based on International Application No. PCT/EP2019/065618, filed Jun. 13, 2019, which was published under PCT Article 21(2) and which claims priority to Luxembourg Application No. 101009, filed Nov. 26, 2018, which are all hereby incorporated in their entirety by reference.

FIELD

The invention relates to the fields of artificial intelligence and computer assisted surgery. In particular, the invention relates to a device and a method for determining 3D representations and relative 3D positions and relative 3D orientations of objects based on an X-ray projection image. The method may be implemented as a computer program executable on a processing unit of the device.

BACKGROUND

In a case in which a bone is fractured, the pieces of the bone may be stabilized by an implant like an intramedullary nail, which may be inserted into the medullary canal of the bone, or a bone plate, which may be affixed to the surface of the bone, as support for the healing of the fracture. The surgical procedure for implanting such implants may be minimally invasive and may require repeated acquisition of X-ray images to enable the surgeon to correctly place the implant. The implant may also be connected to one or more sub-implants, e.g., a screw or a blade.

One particularly difficult step in such a procedure is distal locking. The main difficulty with distal locking using long nails is the nail's bending and torsion as the nail to some extent follows the medullary canal. This prevents a simple static mechanical locking procedure, which is employed in the case of short nails. Free-hand distal locking is challenging and time-consuming and may require acquisition of many X-ray images. For this reason, some manufacturers offer a flexible mechanical solution (hereafter called "long aiming device") that adjusts to the bending of the nail. While a long aiming device simplifies the procedure, its application is still not straightforward because X-ray images showing the long aiming device must be interpreted correctly and the C-arm position adjusted accordingly. Only after correct adjustment of the C-arm may the long aiming device be adjusted properly.

Blau et al. (EP 2801320 A1) proposes a concept where a reference body with metallic markers at a fixed and known position relative to the long aiming device is detected, and the imaging direction onto the reference body is determined. Based on that, the system may give instructions on how to adjust the C-arm imaging device. The disadvantage of such a system is that the X-ray image must contain the reference body. For the adjustment of a long aiming device in case of an antegrade femur nail with locking holes in lateral direction, Blau et al. (US 2013/0211386 A1) uses a reference body in order to determine the bending of the nail in ML direction and in AP direction, respectively.

A state-of-the-art product is described in a video available online: https://otaonline.org/industry-partners/stryker/multimedia/16905832/adapt-for-gamma3.

In addition to a reference body at a fixed position to the long aiming device, this product also requires a reference body attached directly to the X-ray image intensifier.

For example, US 2014/0343572 A1 describes a method for computer assisted determination of values of correction parameters for positioning a medical device relative to a target structure or to a reference base. US 2009/0209851 A1 describes a computer assisted surgical system which processes two or more two-dimensional images of a region of interest, taken at different angles, to produce three-dimensional information associated with the region of interest. WO 2008155772 A1 describes a system for measuring true dimensions and an orientation of objects in a two-dimensional image.

In addition, other objects, desirable features and characteristics will become apparent from the subsequent summary and detailed description, and the appended claims, taken in conjunction with the accompanying drawings and this background.

SUMMARY

It is preferable to work without a reference body because it simplifies product development (e.g., if employing a new implant), is more cost-effective, allows an operating room workflow that more closely resembles the typical workflow, and eliminates the added uncertainties which would be introduced by a mechanical interface for the reference body.

The invention as described herein suggests combining knowledge about the X-ray image generation process with artificial intelligence (in the form of so-called deep morphing and/or the utilization of a neural net) instead of any reference body for providing information needed when performing a treatment of, for example, a fractured bone. It may thus be seen as an object of the invention to provide a device and/or a method enabling 3D representations and relative 3D positions and relative 3D orientations of multiple objects at least partially visible in an X-ray projection image. Here, an object may be any object visible in an X-ray image, e.g. an anatomical structure, an implant, a surgical tool, and/or a part of an implant system.

The term "3D representation" may refer to a complete or partial description of a 3D volume or 3D surface, and it may also refer to selected geometric aspects, such as a radius, an axis, a plane, or the like. The present invention may allow the determination of complete 3D information about the 3D surface or volume of an object, but methods that determine only selected geometric aspects are also considered disclosed with this application.

Throughout this application, the terms "localize" and "localization" mean a determination of the 3D orientation of an object and a determination of the 2D spatial position of the projection of that object onto the image plane. The imaging depth (which is the distance of the object from the image plane), on the other hand, is estimated based on a priori information about typical constellations of objects in the operating room, e.g., relative positions of implant, patient, and imaging device. In this context of this invention, such an estimated imaging depth is sufficient. It is nevertheless possible to determine the imaging depth more precisely in certain cases, as discussed further below.

The present invention may be used to achieve all of the aims of the invention US 2013/0211386 A1, but without any reference body. Using the techniques described in this invention, the long aiming device together with the locking-sleeve configuration may be localized. Based on this, instructions on how to adjust an X-ray imaging device may be given. The imaging depth of the long aiming device may be estimated based on the geometry of a typical distal locking situation in the operating room. Then the distal locking hole may be detected and its 3D position and 3D orientation determined relative to the locking-sleeve configuration and/or the long aiming device.

The actual position of the nail is compared with the projected position of an unbent nail, utilizing the known geometry of the long aiming device and the relative position and orientation of an unbent nail. This allows the computation of the relative 3D position and 3D orientation between the targeted distal locking hole of the (potentially bent) implanted nail and the long aiming device. This considers the fact that the proximal tip of the nail is held in place by the long aiming device. Hence, the possible positions of the tip of the bent nail describe the base of a cone whose vertex is at the proximal tip of the nail. The nail may also be subject to torsion.

A 3D representation and localization of related objects like anatomical structures, implants, surgical tools, and/or parts of implant systems, even if not or only partially visible in the X-ray image, may also be provided. As an example, even if the projection image does not fully depict the femoral head, it may still be completely reconstructed.

It is noted that the image data of the processed X-ray image may be received directly from an imaging device, for example from a C-arm based 2D X-ray device, or alternatively from a data base. Aspects of the invention may also be used to process medical images acquired using other imaging modalities, such as ultrasound or magnetic resonance imaging.

The system suggested in accordance with the invention comprises at least one processing unit configured to execute a computer program product including sets of instructions causing the device (i) to receive an X-ray projection image whose characteristics depend on imaging parameters, (ii) to classify at least one object in the X-ray projection image, (iii) to receive a model of the classified object, and (iv) to determine a 3D representation of the classified object and to localize the classified object with respect to a coordinate system, by matching a virtual projection of the model to the actual projection image of the classified object. This process may consider the characteristics of the X-ray imaging method. In particular, the fact may be considered that the intercept theorem applies, as discussed in the examples later.

The X-ray projection image may represent an anatomical structure of interest a bone. The bone may for example be a bone of a hand or foot, but may in particular be a long bone of the lower extremities, like the femur and the tibia, and of the upper extremities, like the humerus. The image may also include an artificial object like a bone implant being already inserted into or affixed to the imaged anatomical structure of interest.

In the context of the invention, it will be differentiated between an "object" and a "model". The term "object" will be used for a real object, e.g., for a bone or part of a bone or another anatomical structure, or for an implant like an intramedullary nail, a bone plate or a bone screw, or for a surgical tool like a sleeve, k-wire, scalpel, drill, or aiming device, which may be connected to an implant. An "object" may also describe only part of a real object (e.g., a part of a bone), or it may be an assembly of real objects and thus consist of sub-objects. For instance, an assembly of implant and aiming device may be considered to consist of the sub-object "aiming device" and the sub-object "nail", where the object "nail" is subject to bending and the object "aiming device" is not. As another example, the proximal part of a nail may be considered an object, and one of the locking holes of the distal part of a nail may be considered another object.

On the other hand, the term "model" will be used for a virtual representation of an object. For example, a data set defining the shape and dimensions of an implant may constitute a model of an implant. As another example, a 3D representation of an anatomical structure as generated for example during a diagnostic procedure may be taken as a model of a real anatomical object. It should be noted that a "model" may describe a particular object, e.g., a particular nail, or it may describe a class of objects, such as a femur, which have some variability. In the latter case, such objects may for instance be described by a statistical shape or appearance model. It may then be an aim of the invention to find a 3D representation of the particular instance from the class of objects that is depicted in the acquired X-ray image. For instance, it may be an aim to find a 3D representation of the femur depicted in an acquired X-ray image based on a general statistical shape model of femurs. It may also be possible to use a model that contains a discrete set of deterministic possibilities, and the system would then select which one of these best describes an object in the image. For instance, there could be several nails in a database, and an algorithm would then identify which nail is depicted in the image (if this information is not provided by a user beforehand).

Since a model is actually a set of computer data, it is easily possible to extract specific information like geometrical aspects and/or dimensions of the virtually represented object from that data.

The model may include more than one part of an imaged object, with at least one part not being visible in the X-ray projection image. For example, a model of an implant may include a screw intended to be used with an implant, but only the implant is already introduced into an anatomic structure and thus only the implant is visible in the X-ray projection image.

It is also noted that a model may not be a complete 3D model of a real object, in the sense that it only describes certain geometrical aspects of an object, such as the fact that the femoral head can be approximated by a ball in 3D and a circle in the 2D projection image.

The appearance of an object in a projection image may be affected by the X-ray imaging procedure. For example, imaging parameters like the imaging direction relative to gravity, a zoom, the radiation intensity, and/or a presence of a magnetic field may influence the appearance of an object in a projection image. Those or further imaging parameters may cause characteristic changes in the projection image like deformations of the projected object due to a pillow effect, mechanical bending of a C-arm imaging device depending on the imaging direction, a curvature, noise, and/or distortion. Here, those changes are denoted as image characteristics.

It will be understood that it may be possible to determine those image characteristics with a sufficient precision in a projection image. For example, a position of a structure shown in an edge region of the image may be more affected by a pillow effect than a structure in the center of the image. In consequence, the characteristics of a pillow effect may be determined with a sufficient precision based on a structure of known shape that spans from an edge region to a central region. Image characteristics determined for a region in the 2D X-ray may be extrapolated to the entire image.

The effect of the earth's magnetic field on image distortion depends on whether the image intensifier of the C-arm is positioned horizontally or vertically relative to gravity (due to the effect the magnetic field has on the electron beam inside the image intensifier, cf. M. Dotter, "Fluoroskopie-basierte Navigation zur intraoperativen Unterstützung orthopädischer Eingriffe," dissertation, TU Munich, 2004). If the patient positioning (e.g., lateral, left, prone, or supine) is known (e.g., provided as input by a user) and after the imaging direction has been calculated by the system (e.g., using the invention by Blau disclosed in WO 2020/038917A1 entitled Determination of Imaging Direction On A 2D Projection Image which is expressly incorporated by reference herein and hereinafter referred to as "Blau 917"), it may be determined whether the C-arm is positioned horizontally or vertically relative to gravity. This provides a priori information about the effect that the earth's magnetic field has on the distortion in an X-ray image. Another example of a priori information that may be used by the system is the bending of the C-arm imaging device due to gravity.

Another approach to exploit the position of the C-arm may be to obtain an initial measurement of the distortion of images with typical views (e.g., AP and ML) with a respective C-arm position, which can be performed before a patient is opened and then saved by the system. If the position of the C-arm is known (determined using the approach in the previous paragraph), the respective previously determined and saved image characteristics may then be applied to the current image and object match.

Taking into account image and object characteristics as well as the effects of X-ray attenuation, absorption, and deflection, a virtual projection of a model may be deformed and/or distorted like the object is deformed and/or distorted in the X-ray projection image. Such a virtual projection may then be matched to the projection seen in the X-ray image. It will be understood that the matching of the object in the X-ray projection image to the model may include an adaptation of image characteristics of the X-ray projection image to image characteristics of the virtual projection of the model and/or an adaptation of image characteristics of the virtual projection of the model to image characteristics of the X-ray projection image. It is also understood that a match in the 3D projection volume, by minimizing distances in 3D, may also be possible.

The physical dimensions of an object are related to the dimensions of its projection in an X-ray image through the intercept theorem (also known as basic proportionality theorem) because the X-ray beams originate from the X-ray source (the focal point) and are detected by an X-ray detector in the image plane. The precise imaging depth (which is the distance of the object from the image plane) is not generally required in the context of this invention. However, if an object is sufficiently large, the imaging depth may be determined through the intercept theorem, and the larger the object, the more precise this determination will be. Alternatively, the imaging depth may also be determined if the size of the X-ray detector and the distance between image plane and focal point are known. If, for some application, a more precise imaging depth is required, the size of the X-ray detector and the distance between image plane and focal point may be provided by user input or database. The former may also be determined by a calibration step by placing a known object (e.g., nail, k-wire, etc.) directly on the image intensifier/X-ray detector.

According to an embodiment, a deep neural net (DNN) may be utilized for a classification of an object in an X-ray projection image (e.g., proximal part of femur, distal part of femur, proximal part of nail, or distal part of nail, etc.). It is noted that a DNN may classify an object without determining its position (see, e.g., Krizhevsky, A., Sutskever, I., and Hinton, G. E. ImageNet classification with deep convolutional neural networks. In NIPS, pp. 1106-1114, 2012). A neural net may also be utilized for a rough classification of the imaging direction (e.g., AP vs. ML, cf. the paper: Aaron Pries, Peter J. Schreier, Artur Lamm, Stefan Pede, Jürgen Schmidt: Deep morphing: Detecting bone structures in fluoroscopic X-ray images with prior knowledge, 2018, available online at). Such a classification of object and imaging direction may be used to select an appropriate model for following processing steps.

According to an embodiment, the outline of the classified object may be detected in the X-ray image. For objects with variable shape such as anatomical structures, this may proceed by using a "deep morphing" approach as described in the above cited paper by Pries et al. (2018). This paper proposes an approach based on a deep neural network to detect bone structures in fluoroscopic X-ray images. The technique specifically addresses the challenges in the automatic processing of fluoroscopic X-rays, namely their low quality and the fact that typically only a small dataset is available for training the neural network. The technique incorporates high-level information about the objects in the form of a statistical shape model. The technique consists of a two-stage approach (called deep morphing), where in the first stage a neural segmentation network detects the contour (outline) of the bone or other object, and then in the second stage a statistical shape model is fit to this contour using a variant of an Active Shape Model algorithm (but other algorithms can be used as well for the second stage). This combination allows the technique to label points on the object contour. For instance, in the segmentation of a femur, the technique will be able to determine which points on the contour in the 2D X-ray projection image correspond to the lesser trochanter region, and which points correspond to the femoral neck region, etc. Objects described by a deterministic model (e.g., a nail) may also be detected by deep morphing, or simply by a neural segmentation network, as in the first stage of deep morphing.

In a further step, taking into account image and/or object characteristics as well as the effects of X-ray attenuation, absorption, and deflection, a virtual projection of the model may then be adjusted to match the appearance of the object in the X-ray projection image. According to an embodiment, for objects described by a deterministic model, this matching may proceed along the lines described in the paper: Lavallée S., Szeliski R., Brunie L. (1993) Matching 3-D smooth surfaces with their 2-D projections using 3-D distance maps. In: Laugier C. (eds) Geometric Reasoning for Perception and Action. GRPA 1991. Lecture Notes in Computer Science, vol. 708. Springer, Berlin, Heidelberg. In this approach, image characteristics and objects characteristics (in particular, bending and/or torsion of the implanted nail) as well as the effects of X-ray attenuation, absorption, and deflection may be accounted for by introducing additional degrees of freedom into the parameter vector or by using a suitably adjusted model. When modeling the bending of the implanted nail, it may be taken into account that the possible positions of the tip of the bent nail describe the base of a cone whose vertex is at the proximal tip of the nail, with a potential rotation around the nail axis (torsion).

According to an embodiment, for objects described by a statistical shape or appearance model, the matching of virtual projection to the actual projection may proceed along the lines of the following paper: V. Blanz, T. Vetter (2003) Face Recognition Based on Fitting a 3D Morphable Model, IEEE Transactions on Pattern Analysis and Machine Intelligence. In this paper, a statistical, morphable 3D model is fitted to 2D images. For this, statistical model parameters for contour and appearance and camera and pose parameters for perspective projection are determined. It requires an initialization with key points, which may be provided by the result of the deep morphing step. Another approach may be to follow the paper: L. Gu and T. Kanade, 3D alignment of face in a single image, in Proc. of 2006 IEEE Computer Society Conference on Computer Vision and Pattern Recognition. This is a variant of an Active Appearance Model for 2D-3D matching, which also determines position of camera and statistical model parameters.

A neural net may be trained based on a multiplicity of data that is comparable to the data on which it will be applied. In case of an assessment of bone structures in images, a neural net should be trained on the basis of a multiplicity of X-ray images of bones of interest. It will be understood that the neural net may also be trained on the basis of simulated X-ray images. Simulated X-ray images may, for example, be generated from 3D CT data, as described in the appendix of the paper: Aaron Pries, Peter J. Schreier, Artur Lamm, Stefan Pede, Jürgen Schmidt: Deep morphing: Detecting bone structures in fluoroscopic X-ray images with prior knowledge, available online at https://arxiv.org/abs/1808.04441. The realism of simulated X-ray images may be enhanced by using so-called generative adversarial networks (GANs). In this approach, a fully convolutional neural network may receive a simulated image as its input and then returns a refined image. The refinement is learned with an adversarial loss function that rewards a realistic refinement. This is described in the paper: Ashish Shrivastava, Tomas Pfister, Oncel Tuzel, Josh Susskind, Wenda Wang, Russ Webb: Learning from Simulated and Unsupervised Images through Adversarial Training, available online at.

According to an embodiment, more than one neural network may be used, wherein each of the neural nets may specifically be trained for a sub-step necessary to achieve a desired solution. For example, a first neural net may be trained to evaluate X-ray image data so as to classify an anatomical structure in the 2D projection image, whereas a second neural net may be trained to detect the location of that structure in the 2D projection image. A third net may be trained to determine the 3D location of that structure with respect to a coordinate system. It is also possible to combine neural networks with other algorithms, including but not limited to, Active Shape Models. It is noted that a neural net may also learn to localize an object or to determine an imaging direction without the need to first detect the outline of the object in the 2D X-ray image. It is also noted that a neural net may also be utilized for other tasks, e.g., a determination of one or more image characteristics like a pillow effect.

According to an embodiment, an object may also be manually classified and/or identified in the X-ray projection image. Such a classification or identification may be supported by the device by automatically referring to structures that were recognized by the device.

According to an embodiment, the system may compute geometrical aspects of an object (e.g., an axis, an outline, a curvature, a center point), and dimensions of an object (e.g., a length, a radius or a diameter, a distance). This may be accomplished due to the correspondence between the model and the virtual projection that has been matched to the projection seen in the X-ray image.

When displaying the X-ray projection image, geometrical aspects and/or dimensions may be shown as an overlay in the projection image. Alternatively and/or additionally, at least a portion of the model may be shown in the X-ray image, for example as a transparent visualization or 3D rendering, which may facilitate an identification of structural aspects of the model and thus of the imaged object by a user.

It will be understood that sizes may also define a scale suitable for measuring dimensions of and between objects visible in the X-ray projection image. For example, a diameter of a matched object (called "Object A") as indirectly provided by model data, may be utilized for determining a size of other depicted and potentially unknown objects, at least for those objects that can be assumed as positioned at a sufficiently close imaging depth. It may even be possible to calculate a size of a different object (called "Object B") at a different imaging depth based on the intercept theorem if the imaging depth of Object A is known (e.g., because Object A is sufficiently big or because the size of the X-ray detector and the distance between image plane and focal point is known) and if there is information about the differences in imaging depths between Objects A and B (e.g., based on anatomical knowledge).

The present invention provides for a 3D reconstruction and localization of an object whose shape and appearance have some variability. Such objects may for instance be described by a 3D statistical shape or appearance model. This can be done based on a single X-ray image or multiple X-ray images.

Based on one image of an anatomical object, the model is deformed in such a way that its virtual projection matches the actual projection of the object in the X-ray image. Doing so allows a computation of an imaging direction (which describes the direction in which the X-ray beam passes through the object). As an additional plausibility check, the computed imaging direction may then be compared with the imaging direction for the same object that is determined based on the methodology as disclosed in Blau 917, which may take the entire X-ray image (and not just the particular object) into account. This enables a plausibility check because these two imaging directions should not differ.

If multiple X-ray images are acquired, the information from them may be fused (or registered) to increase the accuracy of 3D reconstruction and/or determination of spatial positions or orientations. It is preferable if these X-ray images are acquired from different imaging directions because this may help resolve ambiguities. The more different the imaging directions are (e.g., AP and ML images), the more helpful additional images may be in terms of a determination of 3D information.

For the registration of a pair of X-ray images showing the same object (called "Object C") from two different imaging directions, it may be possible to increase the accuracy of the registration process by taking into account the 3D angle (which may, for instance, be represented by the Euler angles or another suitable representation) between the imaging directions. One way of determining this angle would be to determine the imaging directions as disclosed in Blau 917 for each X-ray image and to compute their difference. Another way may be to utilize another object (called "Object D"), also shown in both images, whose model is deterministic (e.g., a nail connected to an aiming device). By matching the virtual projection of Object D to its actual projection in each X-ray image, the imaging directions for Object D may be determined. This requires that either (i) there be no movement of Object C relative to Object D between acquiring the two X-ray images, or (ii) in case there is a movement, it can be determined as discussed later. This procedure may obviously be extended to register more than two images. This allows a determination of the relative 3D position and 3D orientation between multiple objects depicted in the same X-ray image, even though the imaging depth has not been determined.

The appearance of an object in an X-ray image depends inter alia on attenuation, absorption, and deflection of X-ray radiation, which depend on the object's material. The more material the X-ray beam must pass through, the less X-ray radiation is received by the X-ray detector. This affects not only the appearance of the object within its outline, but it may also change the shape of the outline itself in the X-ray projection image, in particular in areas where the object is thin.

The strength of this effect also depends on the X-ray intensity and the amount of tissue surrounding the object, which the X-ray beam must pass through. The latter depends on the body mass index of the patient and the imaging direction (as disclosed in Blau 917). The amount of soft tissue surrounding the object could be derived from a database, which considers, e.g., ethnicity, gender, body mass index, age.

Object characteristics may also be determined. An object characteristic may for example be a bending and torsion of an intramedullary nail or a fracture of a bone. Those object characteristics may be determined automatically, manually, or semi-automatically, wherein the device may support the manual determination for example by indications of structural aspects which would not be expected when considering only image characteristics (as described above).

On the other hand, object characteristics that are known a priori may be utilized to increase accuracy of localization and determination of 3D representation. An example would be wobbling of connections, e.g., between an implant and an aiming device, which may be described by a model. It is understood that when object characteristics are used in a computation of localization and determination of 3D representation, some characteristics may be weighted more highly than others.

It is noted that a processing unit may be realized by only one processor performing all the steps of the process, or by a group or a plurality of processors, which need not be located at the same place. For example, cloud computing allows a processor to be placed anywhere. For example, a processing unit may be divided into (i) a first sub-processor on which a first neural net is implemented assessing the image data including a classification of anatomical structures like a bone surface, (ii) a second sub-processor on which a second neural net is implemented specialized for determining an imaging direction of the classified anatomical structure, and (iii) a further processor for controlling a monitor for visualizing results. One of these or a further processor may also control movements of, for example, a C-arm of an X-ray imaging device.

According to an embodiment, the device may further comprise storage means providing a database for storing, for example, X-ray images. It will be understood that such storage means may also be provided in a network to which the system may be connected, and that data related to the neural net may be received over that network.

Furthermore, the device may comprise an imaging unit for generating at least one 2D X-ray image, wherein the imaging unit may be capable of generating images from different directions.

The device may further comprise input means for manually determining or selecting a position or part of an object in the X-ray image, such as a bone outline, for example for measuring a distance in the image. Such input means may be for example a computer keyboard, a computer mouse or a touch screen, to control a pointing device like a cursor on a monitor screen, which may also be included in the device.

A computer program may preferably be loaded into the random access memory of a data processor. The data processor or processing unit of a system according to an embodiment may thus be equipped to carry out at least a part of the described process. Further, the invention relates to a computer-readable medium such as a CD-ROM on which the disclosed computer program may be stored. However, the computer program may also be presented over a network like the World Wide Web and can be downloaded into the random access memory of the data processor from such a network. Furthermore, the computer program may also be executed on a cloud-based processor, with results presented over the network.

It has to be noted that embodiments are described with reference to different subject-matters. In particular, some embodiments are described with reference to method-type claims (computer program) whereas other embodiments are described with reference to apparatus-type claims (system/device). However, a person skilled in the art will gather from the above and the following description that, unless otherwise specified, any combination of features belonging to one type of subject-matter as well as any combination between features relating to different subject-matters is considered to be disclosed with this application.

The aspects defined above and further aspects, features and advantages of the present invention can also be derived from the examples of the embodiments to be described hereinafter and are explained with reference to examples of embodiments also shown in the figures, but to which the invention is not limited.

BRIEF DESCRIPTION OF THE DRAWINGS

The present invention will hereinafter be described in conjunction with the following drawing figures, wherein like numerals denote like elements, and.

Figure 1:
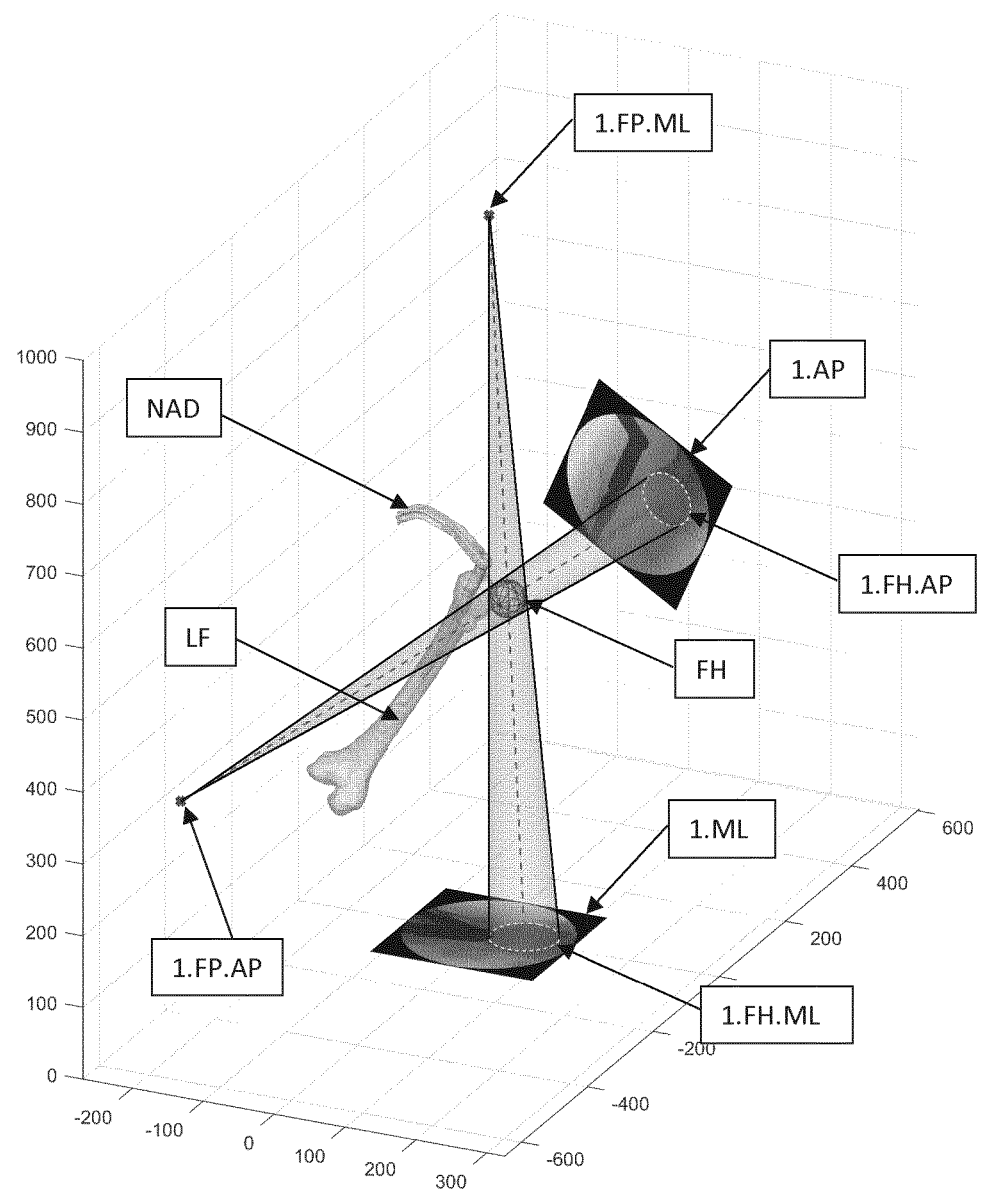
FIG. 1 shows an example for a 3D registration of AP and ML images.

Throughout the drawings, the same reference numerals and characters, unless otherwise stated, are used to denote like features, elements, components, or portions of the illustrated embodiments. Moreover, while the present disclosure will now be described in detail with reference to the figures, it is done so in connection with the illustrative embodiments and is not limited by the particular embodiments illustrated in the figures.

DETAILED DESCRIPTION OF THE EMBODIMENTS

The following detailed description is merely exemplary in nature and is not intended to limit the invention or the application and uses of the invention. Furthermore, there is no intention to be bound by any theory presented in the preceding background of the invention or the following detailed description. 3D Reconstruction Of An Anatomical Object Based On One Image The above cited paper on Deep Morphing by Pries et al. (2018) proposes a method that enables a system to detect (in a 2D projection image) the outline/contour of a bone and label points on the contour. For instance, in the segmentation of a femur, the technique is able to determine which points on the contour in the 2D X-ray projection image correspond to the lesser trochanter, and which points correspond to the femoral neck, etc. Given a 3D statistical shape or appearance model of the same anatomical structure, this model can then be deformed in a way that its virtual projection matches the actual projection in the X-ray image, hence leading to a 3D reconstruction of the anatomical structure and allowing a localization of the object and determination of the imaging direction.

Being able to provide a 3D reconstruction of anatomy based on one X-ray image only is an advantage over the state-of-the-art, which requires the acquisition of at least two images from different viewing directions (typically an AP and an ML image). Moreover, the present invention is also able to determine the 3D orientation of an implant or instrument relative to anatomy based on one X-ray image.

It may hence be possible to localize two objects, at least one of which is an anatomical object, based on one X-ray image depicting these two objects. This means that the only remaining uncertainty is the unknown difference in imaging depth between the two objects.

This allows addressing surgical procedures where acquiring a second image from a different imaging direction is not feasible, e.g., because a fracture is not stable enough.

The accuracy of the 3D reconstruction of an anatomical object may be improved upon by using essential a priori information. This a priori information may be the size or the gender of the patient, but also more anatomy-specific information like geometric information about the anatomical object to be reconstructed. For the example of a 3D reconstruction of a proximal femur based on an ML image, this information may include the length of the femoral neck or the CCD angle. Such information significantly reduces ambiguities in the 3D reconstruction. However, because such information may not be determined with sufficient precision in typical ML images, it may be extracted from AP images that are routinely acquired earlier in the course of the surgery on the proximal femur. The more information is used from earlier images, the more accurate a 3D reconstruction may be. Another way of describing this procedure would be to say that, based on an AP image, a 3D reconstruction of the proximal femur may be performed with typical remaining uncertainties (such as the width of the femoral neck in AP direction), and this 3D reconstruction serves as a priori information or as a starting point for the 3D reconstruction based on a later ML image.

Determination of Relative 3D Position and 3D Orientation Between Objects without Determining the Imaging Depths of any of the Objects As discussed, a precise determination of the imaging depths of localized objects is often not possible. Nevertheless, it is possible to determine the 3D orientation and 3D position of one object relative to another object if there is a priori information about the 3D distance between the two objects.

Example: In case that it is known that the two objects are in contact with each other in physical 3D space, it is possible to determine the relative 3D orientation and relative 3D position among the objects. This can be computed by localizing each object and then virtually moving the model of one of the objects along the vector from the focal point through the center of this object until it touches the model of the other object in virtual 3D space. If the region where the objects are in contact with each other is sufficiently small, this will work even if their projections in the image do not overlap. In the special case where the two projections of the two objects do not overlap in the X-ray image, there is no need to virtually move a model because both models are already positioned at the same imaging depth.

Registration Process of Two or More X-Ray Images from Different Directions

Depending on the bone shape there may be a remaining ambiguity or matching error in the 3D reconstruction based on one image only. This may be alleviated by acquiring a series of images, potentially from different viewing directions, which may be routinely acquired during surgery anyway (e.g. when repositioning the fracture). In general, additional images from different imaging directions are more helpful, and the more different the imaging directions are (e.g., AP and ML images), the more helpful additional images may be in terms of a determination of 3D information. However, even adding images from only slightly different viewing angles, which may be more easily acquired during surgery instead of changing to completely different view (AP to ML or vice versa), may be beneficial.

Finally, another way to increase precision in the matching procedure may be to use preoperative imaging to generate information about the 3D shape of the patient's specific bone, instead of working with general statistical models that describe the variability of bones.

The invention allows to register multiple X-ray images of at least one common object taken from different directions. This is important because 3D registration allows a determination of relative 3D positions between multiple objects without an explicit determination of the imaging depth.

For the 3D reconstruction of an object of variable shape (typically an anatomical structure described, e.g., by a statistical shape or appearance model and called "Object F" in this section) based on two or more X-ray images, the procedure outlined above for one image may be extended to two or more images. That is, Deep Morphing may be used to detect the contour of Object F and label points on its contour in each 2D X-ray image. Given a 3D statistical shape model of Object F, this model can then be deformed in a way that its virtual projections simultaneously match the actual projections of Object F in two or more X-ray images as closely as possible. This procedure does not need a priori information about the imaging directions because it implicitly determines the imaging direction for each X-ray image.

As an alternative for the registration of a pair of X-ray images taken from two different imaging directions, it may be possible to increase the accuracy of the registration process by taking into account the 3D angle between the imaging directions, which may be determined using two different procedures. The more precisely this angle can be determined, the more precise the 3D registration may be.

One way of determining this angle would be to determine the imaging directions as disclosed in Blau 917 for each X-ray image and to compute their difference. Another way may be to utilize another object in the X-ray image (called "Object G") whose model is deterministic (e.g., a nail connected to an aiming device). By matching the virtual projection of Object G to its actual projection in each X-ray image, the imaging directions for Object G may be determined.

If the 3D angle between imaging directions computed from Object G differ significantly from the 3D angle between imaging directions for Object F, this could indicate, for instance, that Object G's position relative to Object F has changed between acquiring the images (e.g., there has been a rotation around the nail axis). It may be possible to automatically correct for such a movement; if this is not possible, no 3D registration should be attempted. If the angles determined by the two procedures are sufficiently close, the results could be weighted and averaged (with a weighting depending, e.g., on image quality, detection quality, visibility, 3D reconstruction uncertainties), and a 3D registration may be performed. This procedure may obviously be extended to register more than two images.

In the following, the influence of C-arm width, size of image detector, zoom, etc. on a 3D registration will be illustrated with examples. It is shown that in all of these examples determination of imaging depth is not required.

Influence of C-arm width: FIG. 1 depicts the left femur (denoted LF) and the nail implant with attached aiming device (denoted NAD). Furthermore, it shows the AP X-ray image (denoted 1.AP) and ML X-ray image (denoted 1.ML) and their corresponding focal points (denoted 1.FP.AP and 1.FP.ML). The 3D ball approximates the femoral head (denoted FH), and the dashed white circles are its 2D approximated projections in the images (denoted 1.FH.AP and 1.FH.ML). The C-arm has a width (here defined as the distance between focal point and image plane) of 1000 mm. The cones indicate the part of the X-ray beam passing through the femoral head. It is noted that throughout this application, we follow the convention to call images taken in a posterior-anterior direction "AP" images, and images taken in an anterior-posterior direction "PA" images. Similarly, we call images taken in lateral-medial direction "ML" images, and images taken in medial-lateral direction "LM" images.

Figure 2:
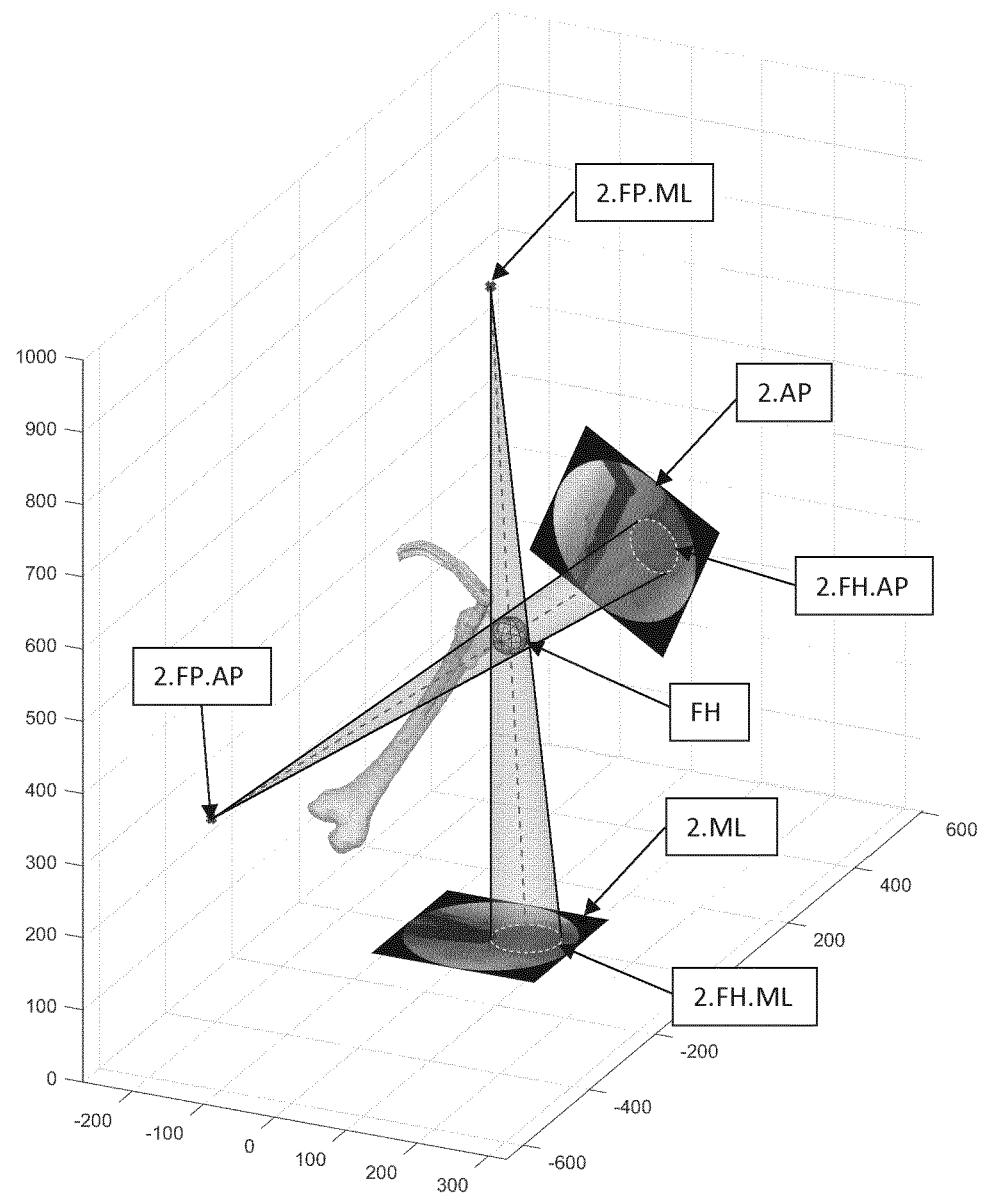
FIG. 2 shows an example for a 3D registration of AP and ML images and illustrates the effect of an incorrectly estimated C-arm width.

In FIG. 2, instead of the true 1000 mm, the C-arm width was incorrectly estimated as 900 mm. Hence, all objects in the image, including the femoral head (FH), appear smaller in the X-ray images than they should. Therefore, it seems as if the objects were shifted towards the AP image plane (denoted 2.AP) as well as towards the ML image plane (denoted 2.ML). The corresponding focal points are denoted 2.FP.AP and 2.FP.ML. A 3D reconstruction of the femoral head (FH) based on the 2D projections of the approximated femoral head (white circles 2.FH.AP and 2.FH.ML) remains unchanged compared to FIG. 1. The only parameter that is changed is the apparent imaging depth. The imaging depth, however, is not relevant in this scenario because the relative 3D position of femoral head and nail has not changed.

Figure 3:
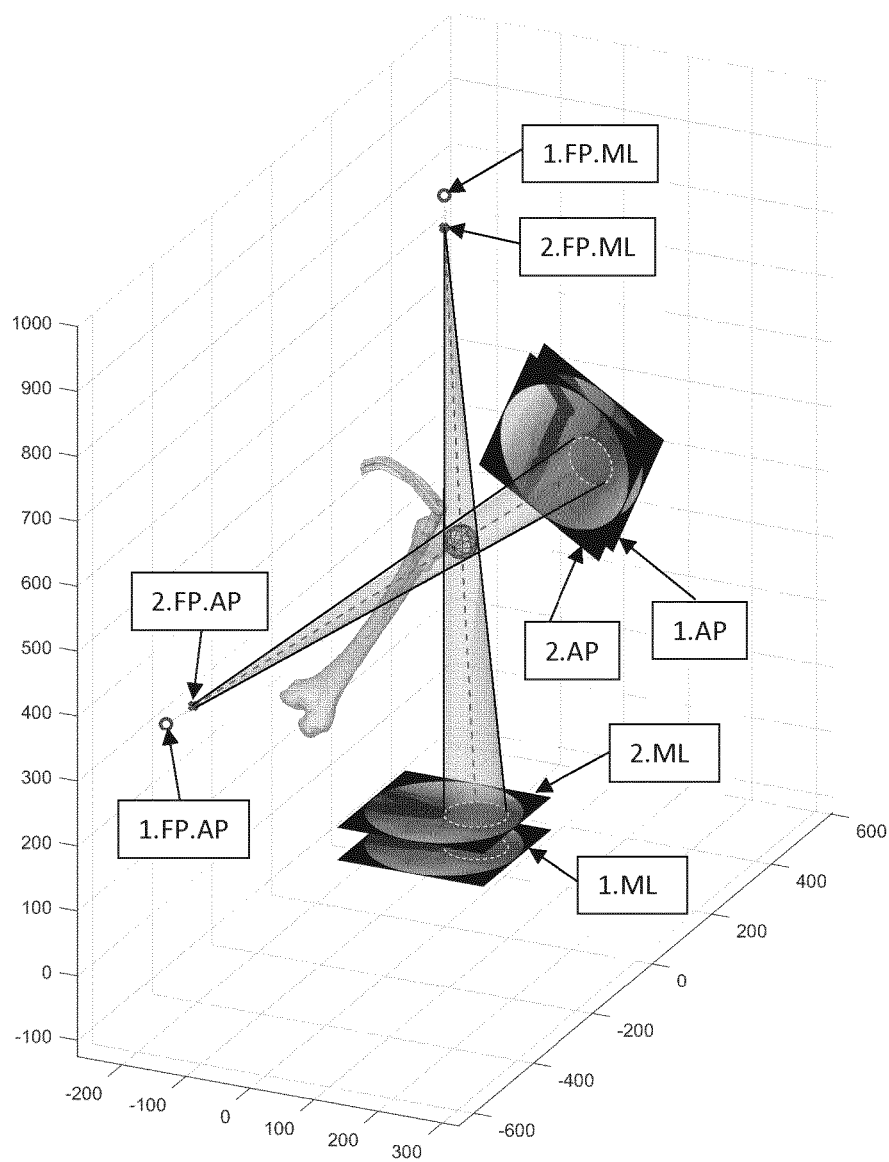
FIG. 3 compares the situations of FIGS. 1 and 2.

In order to illustrate that the only difference between FIG. 1 and FIG. 2 is the apparent imaging depth, FIG. 3 shows both scenarios simultaneously.

Figure 4:
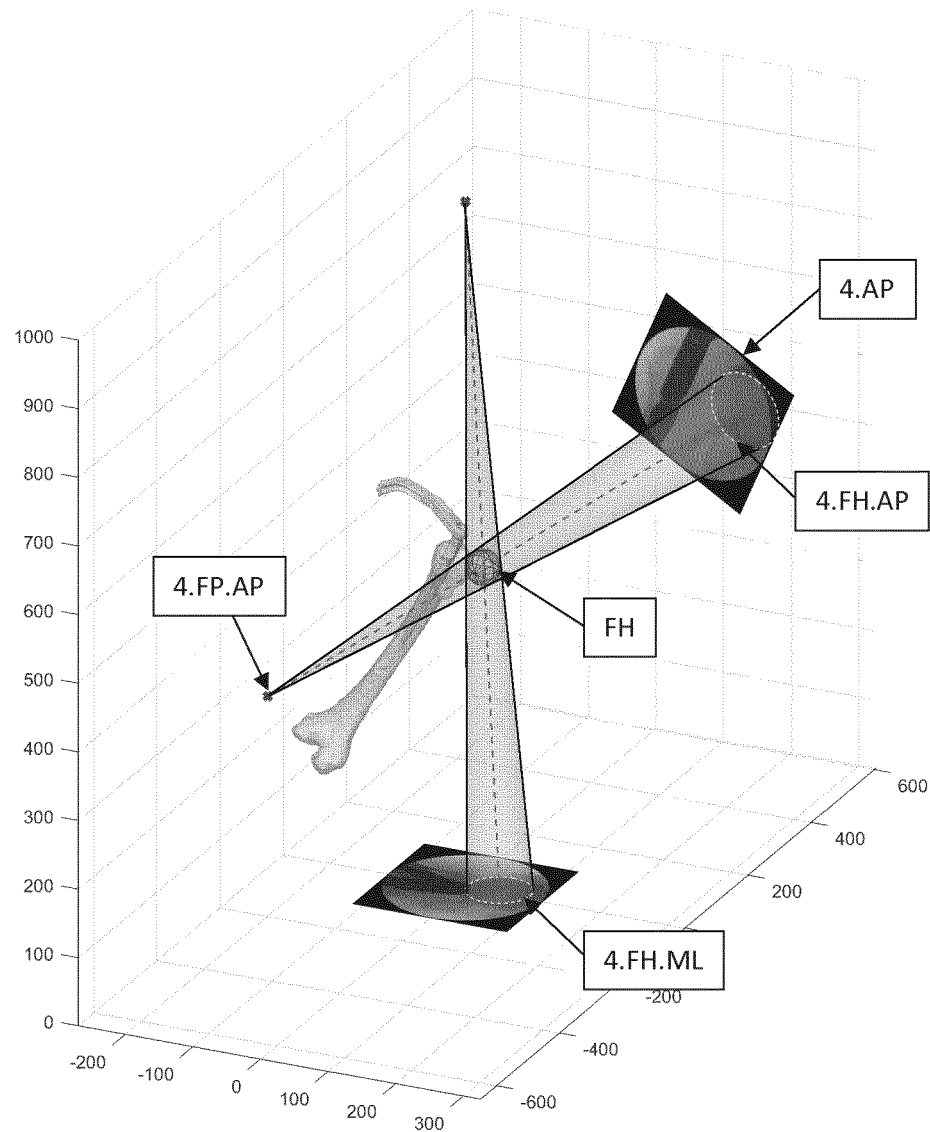
FIG. 4 shows an example for a 3D registration of AP and ML images and illustrates the effect of a zoom.
Figure 5:
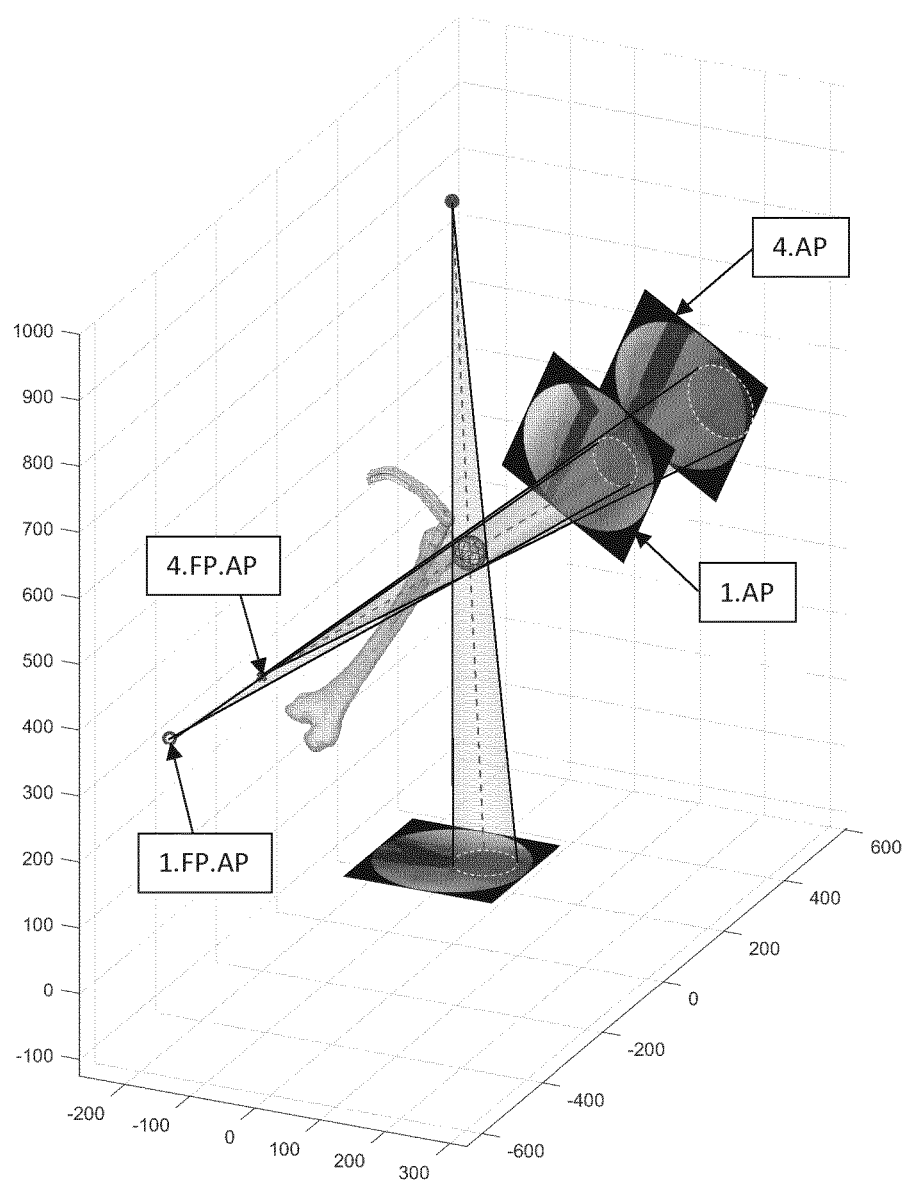
FIG. 5 compares the situations of FIGS. 1 and 4.

Influence of zoom: If one of the images was captured with a zoom factor, the objects appear bigger than without zoom. For FIG. 4, the AP image (denoted 4.AP) was captured with a zoom factor of 1.5. Hence, all objects in the image, including the femoral head (FH), seem as if they had been moved towards the focal point in AP (denoted 4.FP.AP). As before, a 3D reconstruction of the femoral head (FH) based on the 2D projections of the approximated femoral head (dashed white circles 4.FH.AP and 4.FH.ML) remains unchanged compared to FIG. 1. The only parameter that is changed is the apparent imaging depth. The imaging depth, however, is not relevant in this scenario because the relative 3D position of femoral head and nail has not changed. Analogous comments apply when both images have a zoom. FIG. 5 compares the situation with zoom (as in FIG. 4) and without zoom (as in FIG. 1).

Figure 6:
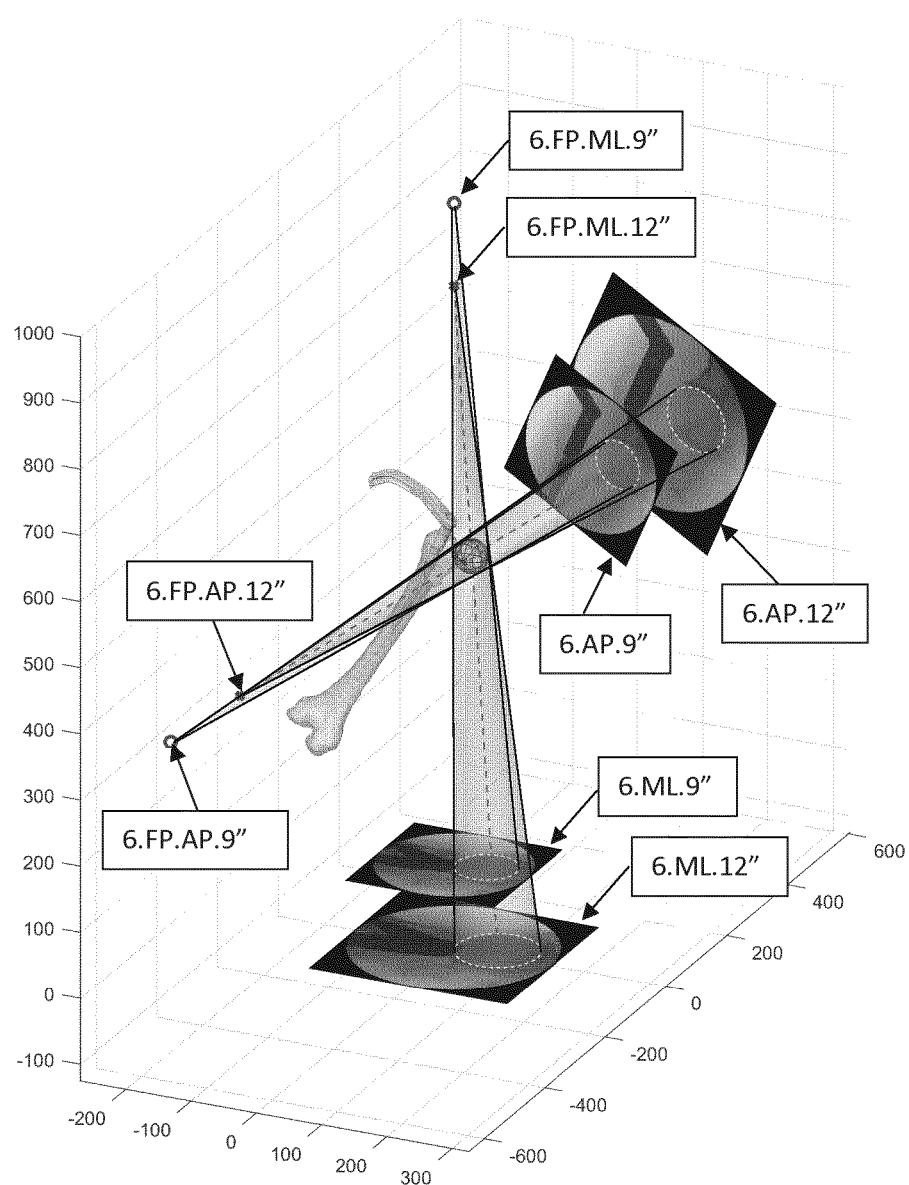
FIG. 6 shows an example for a 3D registration of AP and ML images and illustrates the effect of the X-ray receiver size.

Influence of size of X-ray detector: If the assumed size of the X-ray detector is 12" instead of the true 9", the objects appear bigger in the image, and it seems as if the objects had been moved towards the focal points in both images. This is shown in FIG. 6, where:

6.AP.9" refers to the AP image with 9" X-ray detector with focal point denoted 6.FP.AP.9"
6.AP.12" refers to the AP image with 12" X-ray detector with focal point denoted 6.FP.AP.12"
6.ML.9" refers to the ML image with 9" X-ray detector with focal point denoted 6.FP.ML.9"
6.ML.12" refers to the ML image with 12" X-ray detector with focal point denoted 6.FP.ML.12"

The effect is equivalent to a zoom factor that is applied to both images. Hence, the same conclusions as in the case of zoom may be drawn.

Influence of gravity on ML images: When capturing ML images with a C-arm based X-ray imaging device, the focal point moves towards the floor by 8 mm according to the dissertation by Dotter (2004). With a given C-arm width of 1000 mm, this corresponds to a rotation of the C-arm by approximately 1 degree. This rotation causes a vertical shift and a small rotation of the objects depicted in the image.

Since the shift and rotation is detected during the reconstruction of the scene (based on the estimated location of the implant), neglecting this effect causes a small error with respect to the center of the reconstructed femoral head. Moreover, it is possible to consider the gravity effect during reconstruction to avoid this error.

Measuring a Feature of a Classified Object

The current invention does not require an a priori calibration. Measurements may be performed in mm if there is a known object in the image located in the vicinity of (at a similar depth as) the structure to be measured. Since the known object has known dimensions, it can be used for calibrating measurements. This is similar to the procedure proposed by Baumgaertner et al. to determine a TAD value (cf. Baumgaertner M R, Curtin S L, Lindskog D M, Keggi J M: The value of the tip-apex distance in predicting failure of fixation of peritrochanteric fractures of the hip. J Bone Joint Surg Am. 1995, 77: 1058-1064).

Example 1: A nail has been inserted, and an AP image is available. The nail has been identified and localized. Since the nail is located in the middle of the shaft and thus at a similar imaging depth as the depicted lateral cortex of the shaft, the known nail geometry can be used for calibration. This allows to provide a scaling for determining the distance between the nail axis and the lateral cortex of the shaft.

Example 2: It may even be possible to calculate a size of a different object (called "Object B") at a different imaging depth based on the intercept theorem if the imaging depth of Object A is known (e.g., because Object A is sufficiently big or because the size of the X-ray detector and the distance between image plane and focal point is known) and if there is information about the differences in imaging depths between Objects A and B (e.g., based on anatomical knowledge).

Handling Image Distortion for the Example of an Intramedullary Nail

In general, there are two ways of handling distortion of images:
1. Deemphasizing regions in the X-ray image where distortion is known to be strong (e.g., border of images), placing more emphasis on regions less affected by distortion
2. Determining distortion and accounting for it
These will now be illustrated at the example of an AP image of a femur with inserted nail.

Figure 9:
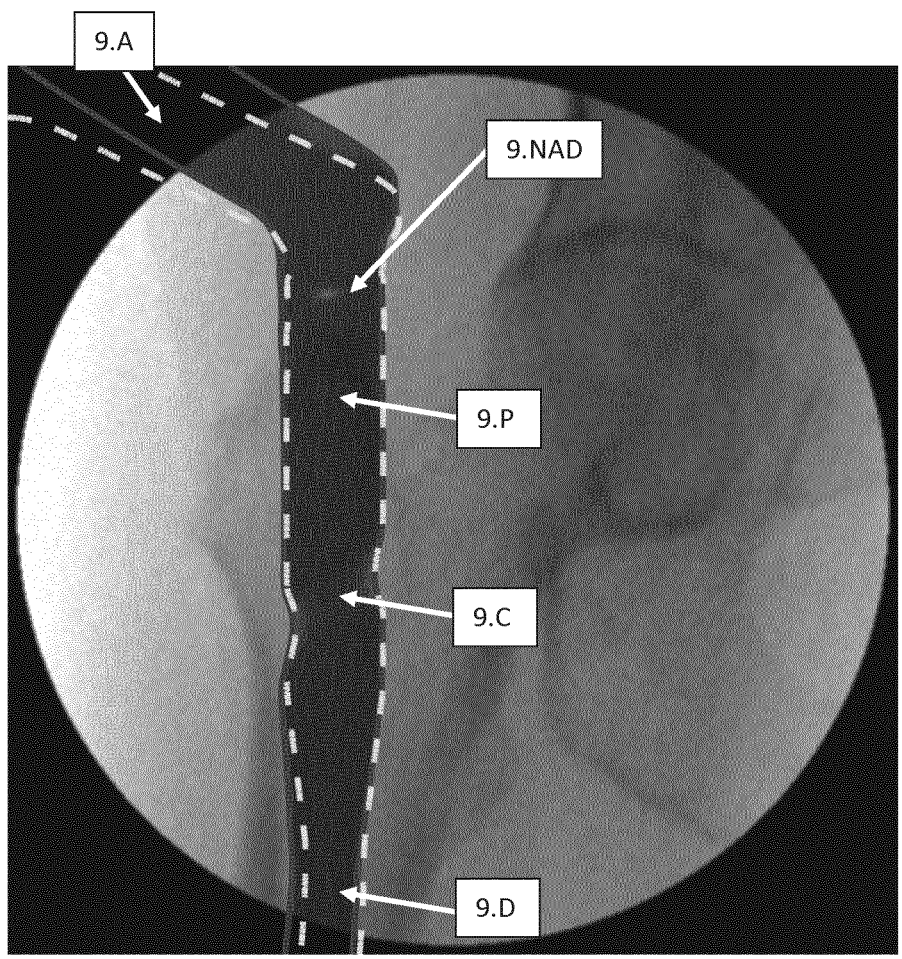
FIG. 9 compares FIGS. 7 and 8.

Re 1. The following letters are used in the labeling of FIG. 9. The solid line is the contour of a nail and aiming device as seen in a distorted X-ray image. The white dashed line shows the hypothetical outline of the nail and aiming device as they would be shown in an image without distortion.
 a. 9.D: Distal part of intramedullary nail
 b. 9.C: Central part of nail, including hole for neck screw
 c. 9.P: Proximal part of intramedullary nail
 d. 9.A: Aiming device Typically, 9.D is located in a more distorted region of the X-ray image. Moreover, the precise location of 9.D is not as important when forecasting a trajectory for a screw inserted through the hole at 9.C. Thus, in a forecast of a screw trajectory, the locations of 9.C and 9.P may receive a higher weighting than 9.D, where the exact weighting may be determined based on their visibility and reliability of detection. A higher weighting on 9.C and 9.P may also be justified because these regions are closer to the region of interest (the screw hole and femoral head). Moreover, the appearance of 9.C carries information about the rotation of the nail around its axis.

Re 2. Distortion in an image may be determined by:
 i. surgeries performed earlier (could be learned for a specific C-arm)
 ii. calibration before surgery: a known object (e.g., nail, k-wire, etc.) could be placed directly on the image intensifier/X-ray detector at a known distance to the image plane. This may also be used for determining the size of the X-ray detector and the distance between focal point and image plane.
 iii. images acquired earlier (could be learned by an algorithm during a surgery)
 iv. a database with typical distortion effects (e.g., typical pillow effect, earth's magnetic field, for typical C-arm positions). The device may use the knowledge that digital X-ray machines do not distort.

If such information is available, it may be utilized when matching a virtual projection of a model to a projection in the X-ray image. The distortion may be applied to the entire image, or specifically to the shape that is being matched.

The distortion depends strongly on the position of the C-arm imaging device in physical space, due to the earth's magnetic field. In a typical operating room setting, the position of the C-arm imaging device may be obtained from the imaging direction if the positioning of the patient (e.g., prone or supine) is known. The imaging direction in turn may be determined, e.g., as disclosed in Blau 917.

Figure 7:
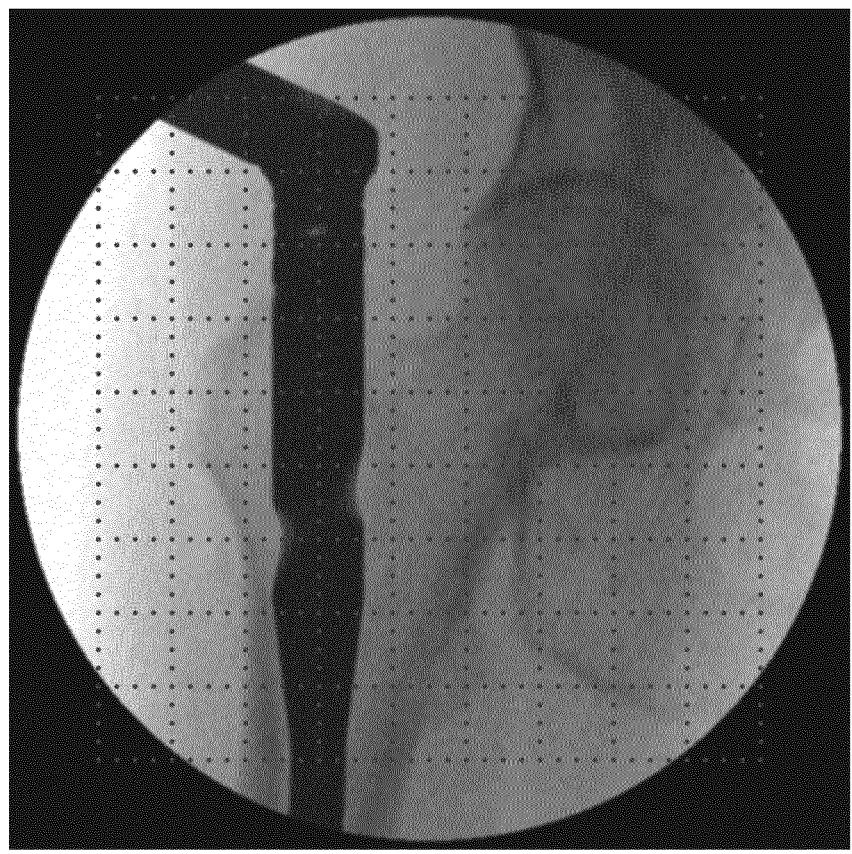
FIG. 7 shows an undistorted proximal AP X-ray of a femur with nail and aiming device.

In the following, an example of the pillow effect in the case of an AP image of the proximal femoral nail is discussed. FIG. 7 depicts a typical AP image without distortion, as can be seen from the dotted rectangular grid.

Figure 8:
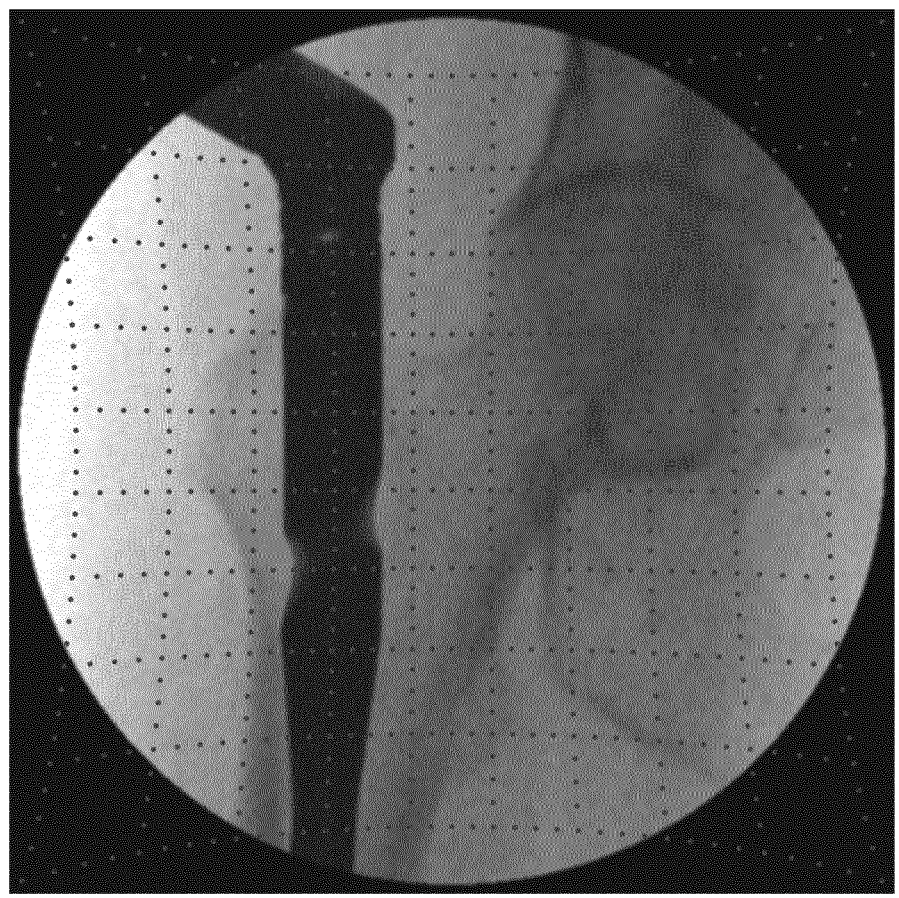
FIG. 8 shows a distorted proximal AP X-ray of a femur with nail and aiming device.

FIG. 8 shows the same scene with a simulated pillow effect distortion. This is the distortion type that has the biggest influence on AP images, according to the dissertation by Dotter (2004). The distortion can be seen from the distorted dotted grid. It is clearly visible that pixels in the vicinity of the image borders are more affected than pixels in the image center.

FIG. 9 again shows the same distorted image as in FIG. 8, but without the grid. The solid line is the contour of the nail and aiming device as seen in the X-ray image (denoted by 9.NAD). The white dashed line shows the hypothetical outline of the nail and aiming device, as they would be shown in an image without distortion.

In the following, an example of sinusoidal distortions is discussed in the case of an ML image of the proximal femoral nail. According to the dissertation of Dotter (2004), ML images suffer from sinusoidal distortion (due to the earth's magnetic field) in addition to the pillow effect. The pillow effect may be determined based on an AP image, and then a correction may be applied to an ML image. Assuming that this correction is correct, only a sinusoidal distortion would remain in the ML image.

Figure 10:
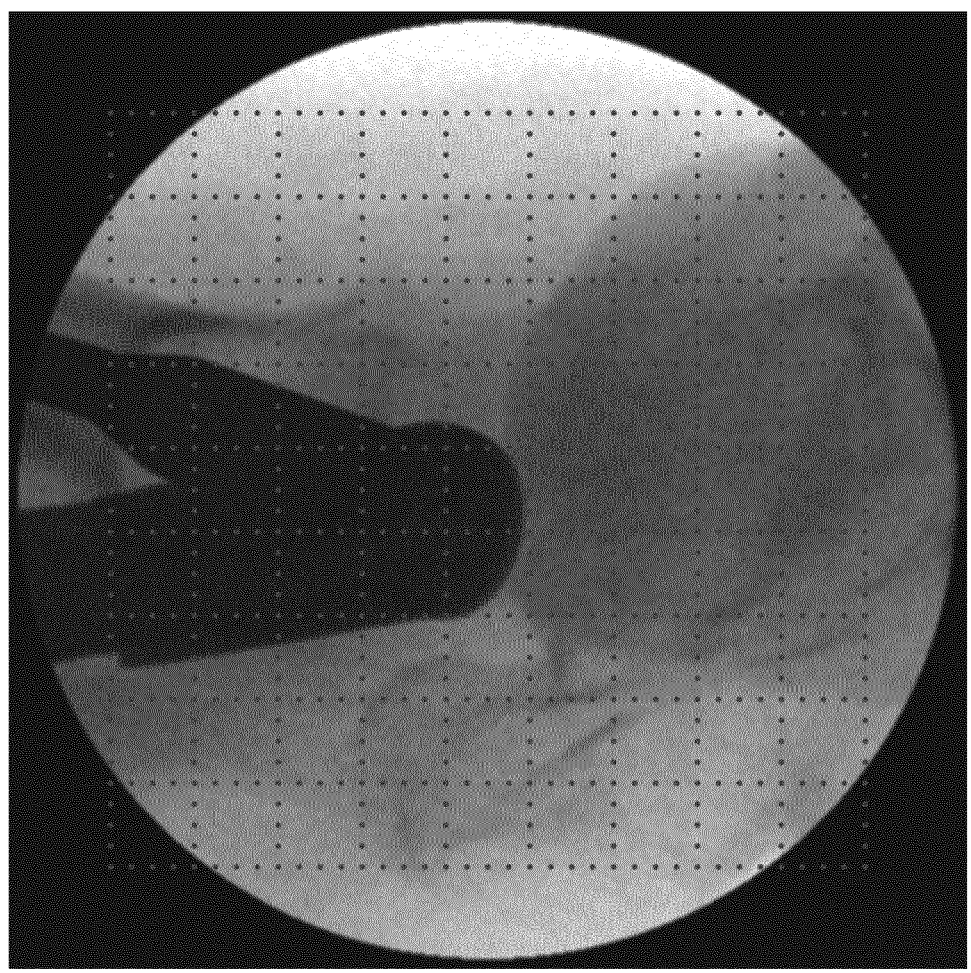
FIG. 10 shows an undistorted proximal ML X-ray of a femur with nail and aiming device.
Figure 11:
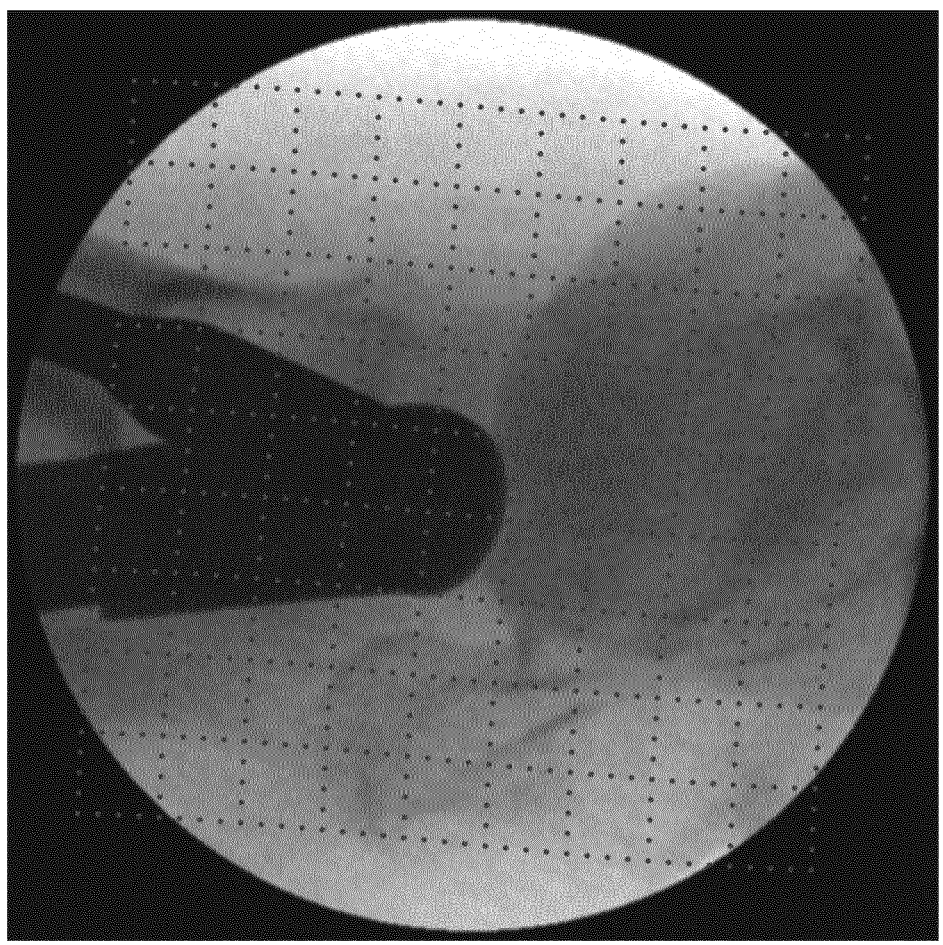
FIG. 11 shows a distorted proximal ML X-ray of a femur with nail and aiming device.

FIG. 10 depicts an ML image without distortion, as can be seen from the dotted rectangular grid. FIG. 11 shows the same scene with sinusoidal distortion, as can been seen from the distorted grid.

Figure 12:
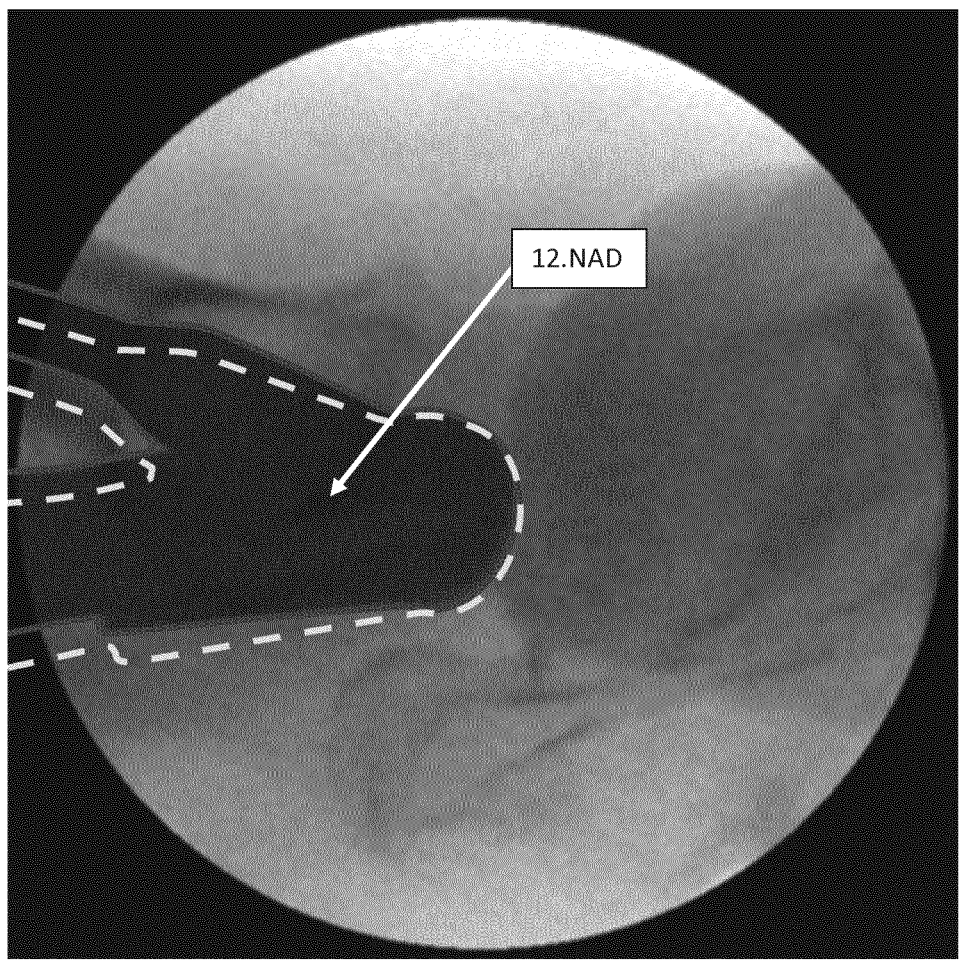
FIG. 12 compares FIGS. 10 and 11.

FIG. 12 again shows the same distorted image as in FIG. 11, but without the grid. The solid line is the contour of the nail and aiming device as seen in the X-ray image (denoted by 12.NAD). The white dashed line shows the hypothetical outline of the nail and aiming device, as they would be shown in an image without distortion.

Figure 13:
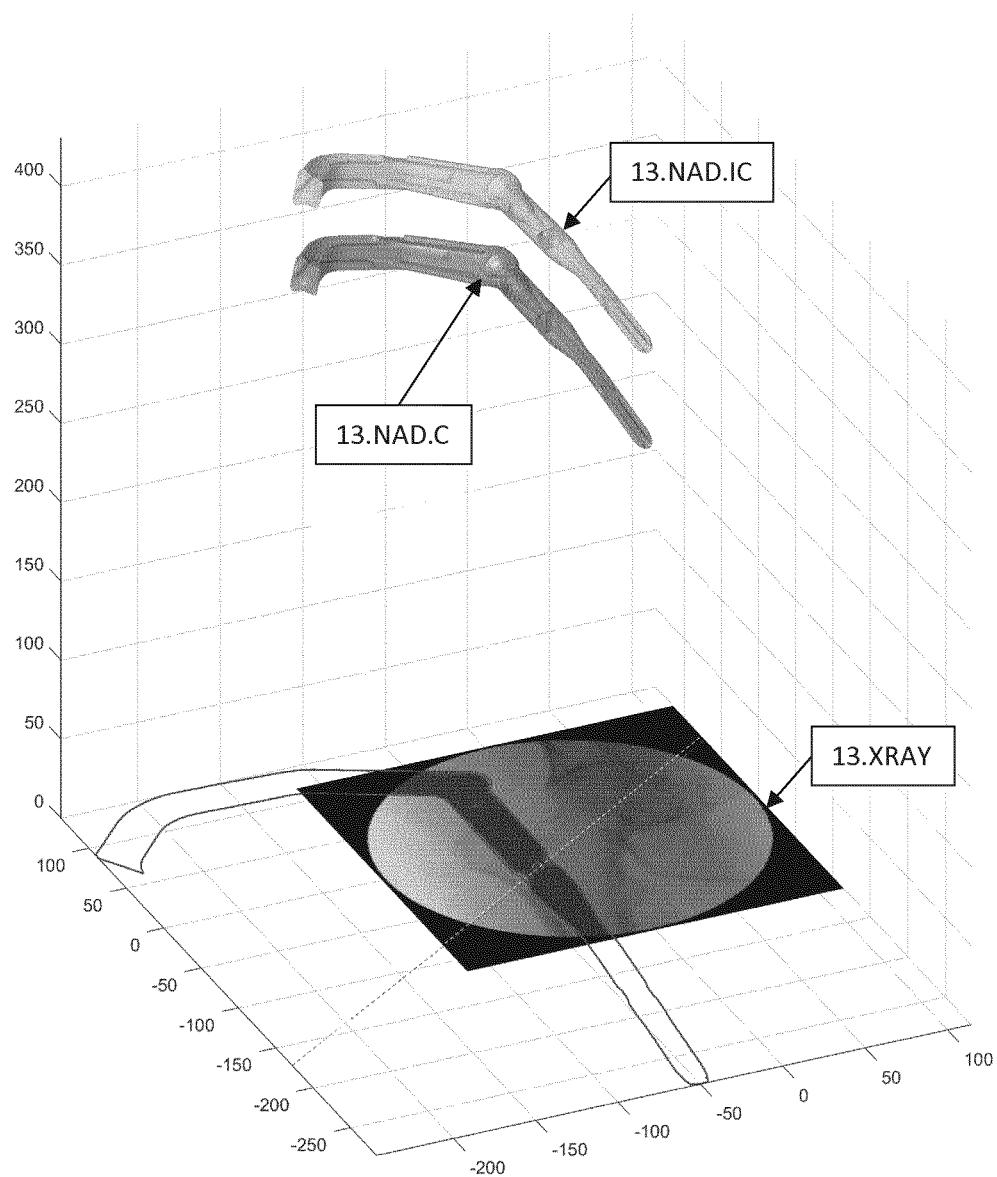
FIG. 13 illustrates the effect that ignoring distortion has on the localization of the nail and aiming device.

FIG. 13 shows the consequences of localizing the nail and aiming device based on a distorted X-ray AP image of the proximal femur. The X-ray projection image 13.XRAY is the same as the one depicted in FIG. 9. If distortion is not taken into account, this would lead to a localization of the nail and aiming device at the incorrect position indicated by 13.NAD.IC, whereas the correct location would be at the position indicated by 13.NAD.C. While the incorrectly determined imaging depth is not relevant in the context of this invention, the incorrect 3D orientation on the other hand is problematic. In the shown situation, there is an error of approximately 4.5 degrees with respect to the nail axis.

Figure 14:
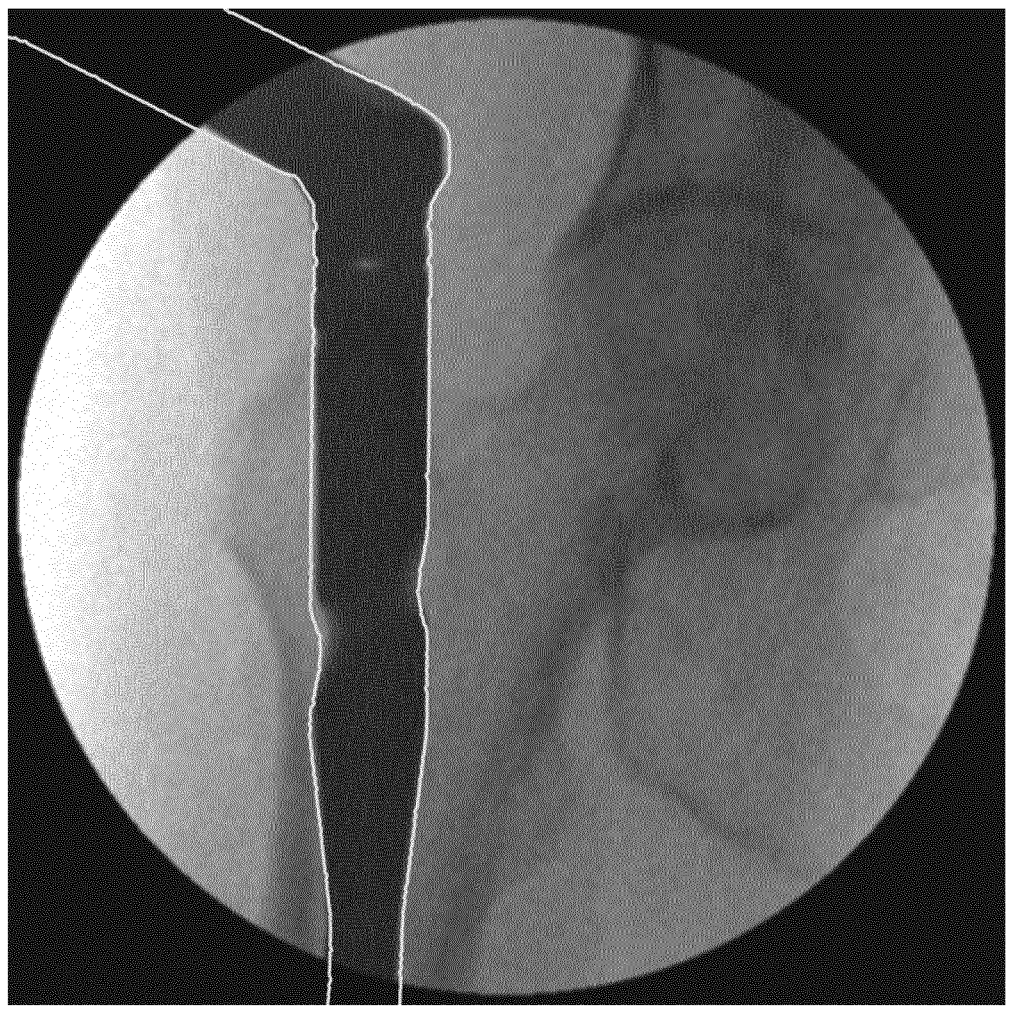
FIG. 14 shows an incorrect 2D match of the outline of nail and aiming device.
Figure 15:
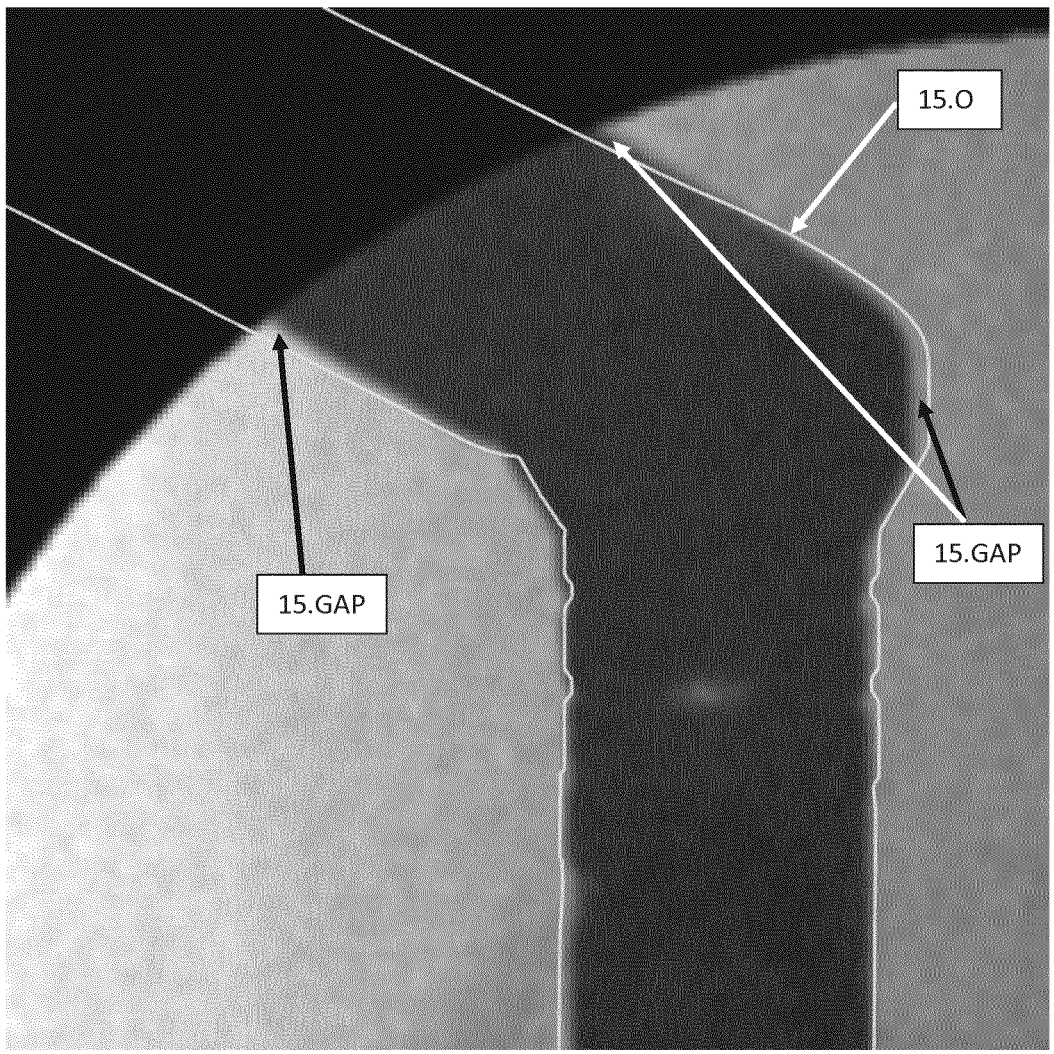
FIG. 15 is a zoom of part of FIG. 14.
Figure 16:
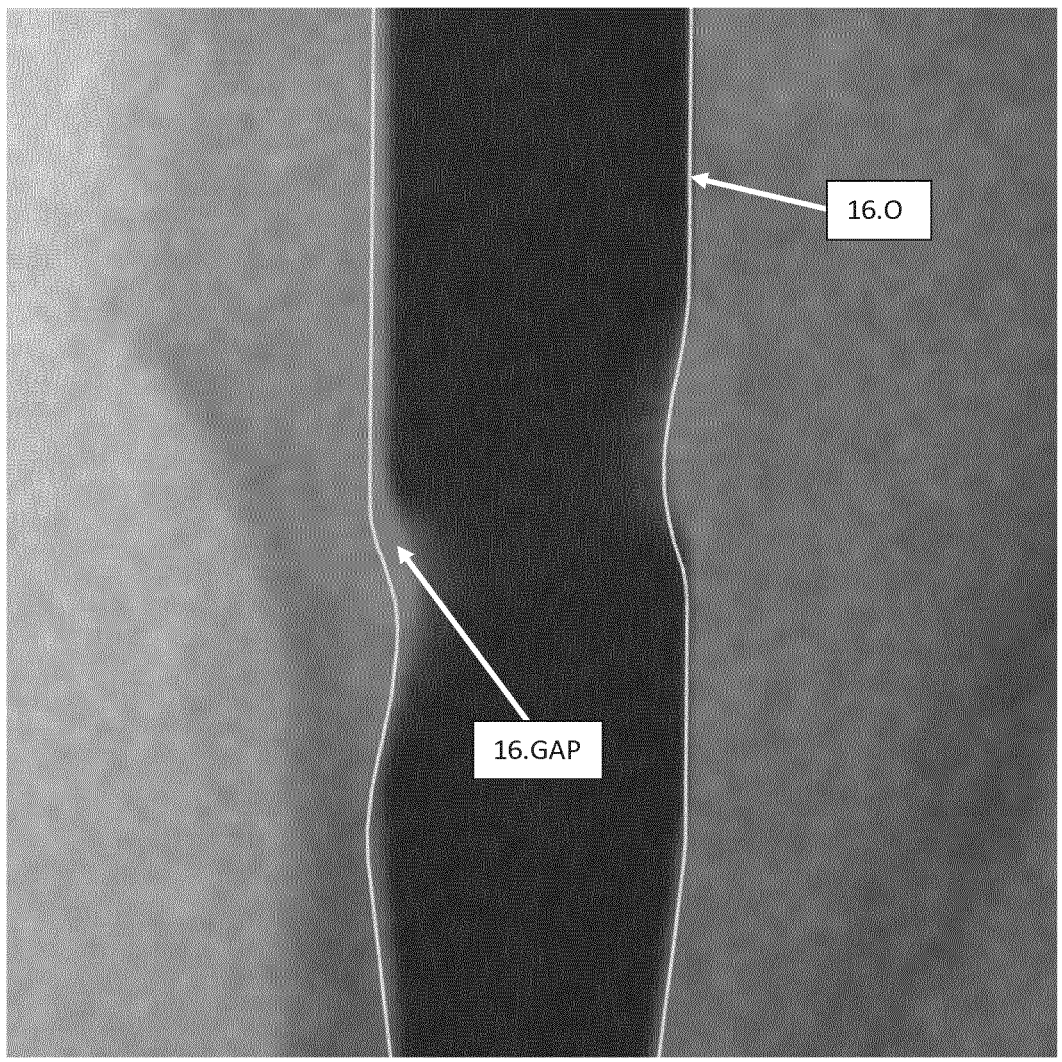
FIG. 16 is a zoom of part of FIG. 14.

However, FIG. 14 shows that the match of the 2D outline in the corresponding X-ray image (the solid white line) that leads to the incorrect localization in FIG. 13 is itself only a poor match of the true outline. This can be more clearly seen when zooming into the image, as is shown in FIG. 15 and FIG. 16. For instance, in FIG. 15, there are clearly several gaps between the nail appearing in black and the determined outline (the solid white line, denoted 15.O), some of which are indicated by 15.GAP. Moreover, in FIG. 16, there is also clearly a gap visible between the nail appearing in black and the determined outline (the solid white line, denoted 16.O), in particular at the nail hole, as indicated by 16.GAP. The gap 16.GAP is explained by an incorrectly determined nail rotation. By combining the two methods described above (focus on less distorted region around the nail hole and taking into account the type of the expected distortion especially in the border of the image where the aiming device is located) the accuracy of localization may significantly be improved. The present invention allows for an interaction between dewarping and matching process, leading to more precise results.

Handling an Exchange of the Positions of X-Ray Source and Receiver

Because X-ray imaging devices allow mirroring of images and this invention does not use a calibration reference body attached to the image detector throughout the surgery, an exchange of the positions of X-ray source and receiver may not be detected, even if the treatment side (left or right bone) is known. A user could be required to provide information about whether or not the mirroring function is activated. If this is not desired, in the following, situations are discussed how a correct 3D reconstruction of the scene is nevertheless possible.

Figure 17:
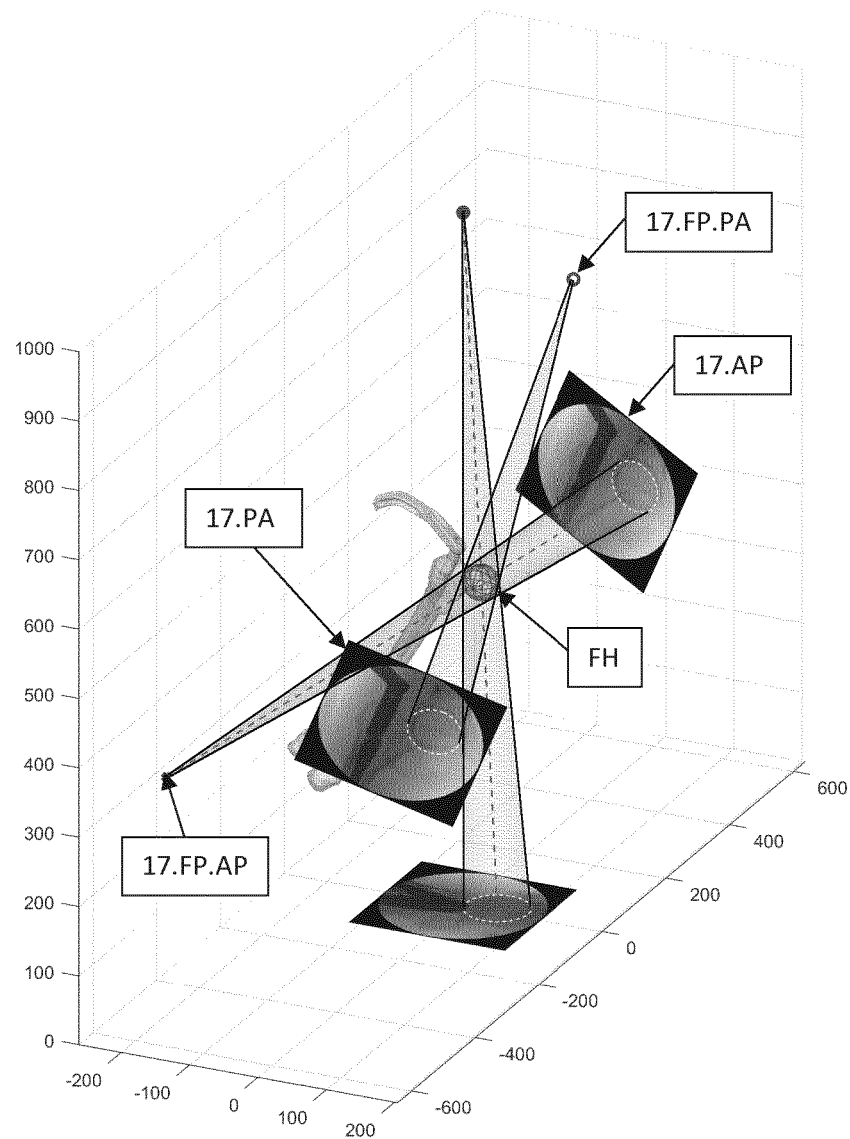
FIG. 17 shows an example for a 3D registration of AP and ML images and illustrates the effect of receiving a PA image instead of an AP image.

In case of a proximal AP image of the femur or humerus, an exchange of the positions of X-ray source and receiver cannot be detected, but such an exchange has no significant effect on a correct 3D reconstruction due to symmetries of proximal femur or humerus. FIG. 17 shows the scene from FIG. 1, where the original imaging direction is AP with focal point 17.FP.AP, leading to AP image denoted 17.AP. In addition, FIG. 17 also shows a PA image, denoted 17.PA, which is an approximate mirror image of 17.AP (it is to be noted that in the figure, the image 17.AP is shown from the front, and the image 17.PA from the back). The image 17.PA is generated by the C-arm if its focal point is at location 17.FP.PA. In the 3D scene, the PA configuration is obtained from the AP configuration by mirroring with respect to the plane defined by femur shaft axis and femoral head center. It can be seen that both AP and PA images will lead to the same 3D reconstruction of the femoral head (FH).

Figure 18:
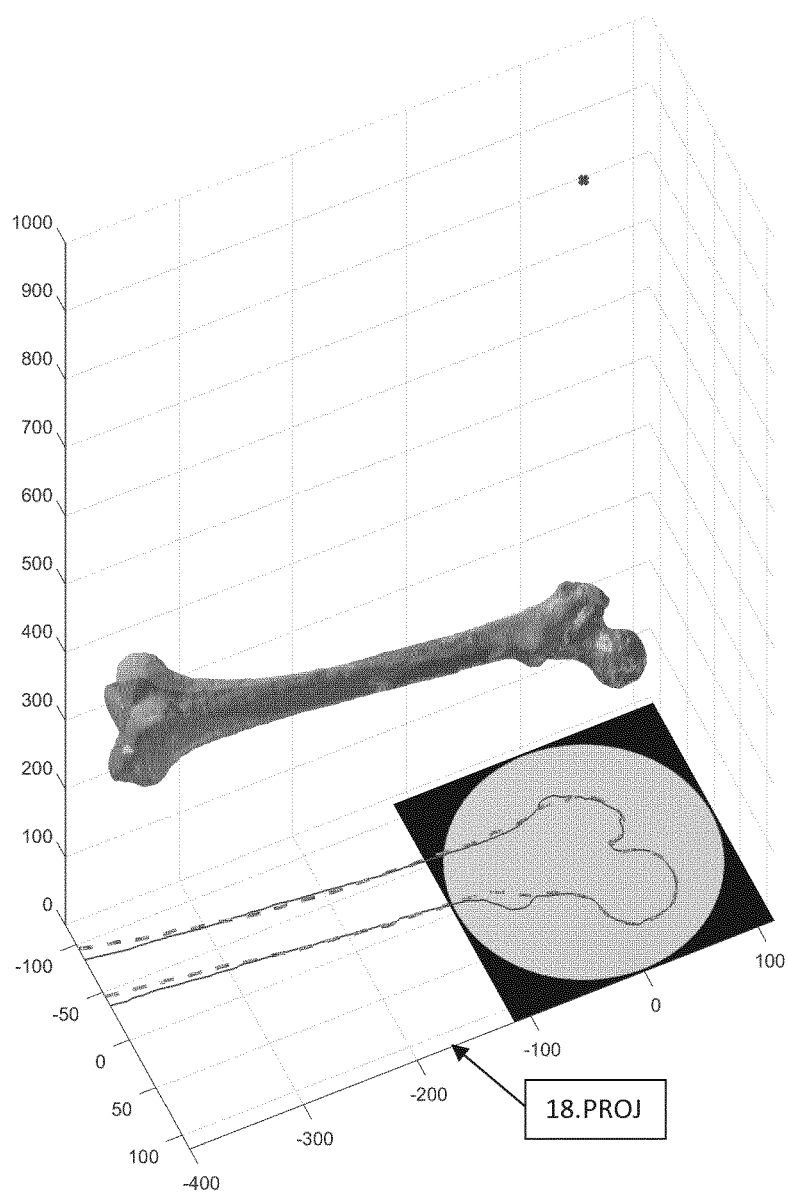
FIG. 18 illustrates the effect of receiving a PA image instead of an AP image in the projection plane.

The explanation is that the nail implant looks very similar from either AP or mirrored PA direction when keeping it at a fixed distance from the image plane. Furthermore, the proximal femur has a certain symmetry. For instance, if a mirrored image is received, it would be concluded that the other side is being treated (e.g., right instead of left) if the current C-arm orientation is kept. However, the projected 2D outlines of both bones (i.e., left and right) are quite similar. FIG. 18 illustrates this statement. It shows a typical AP imaging scenario for a left femur. It also depicts the right femur at the same imaging depth. For both left and right bones, the outline of the nail implant in the 2D projection plane (denoted 18.PROJ) would be essentially identical. Moreover, the 2D bone outlines in the 2D projection plane differ only slightly, as can be seen by comparing the dashed and solid lines in the plane 18.PROJ.

Figure 19:
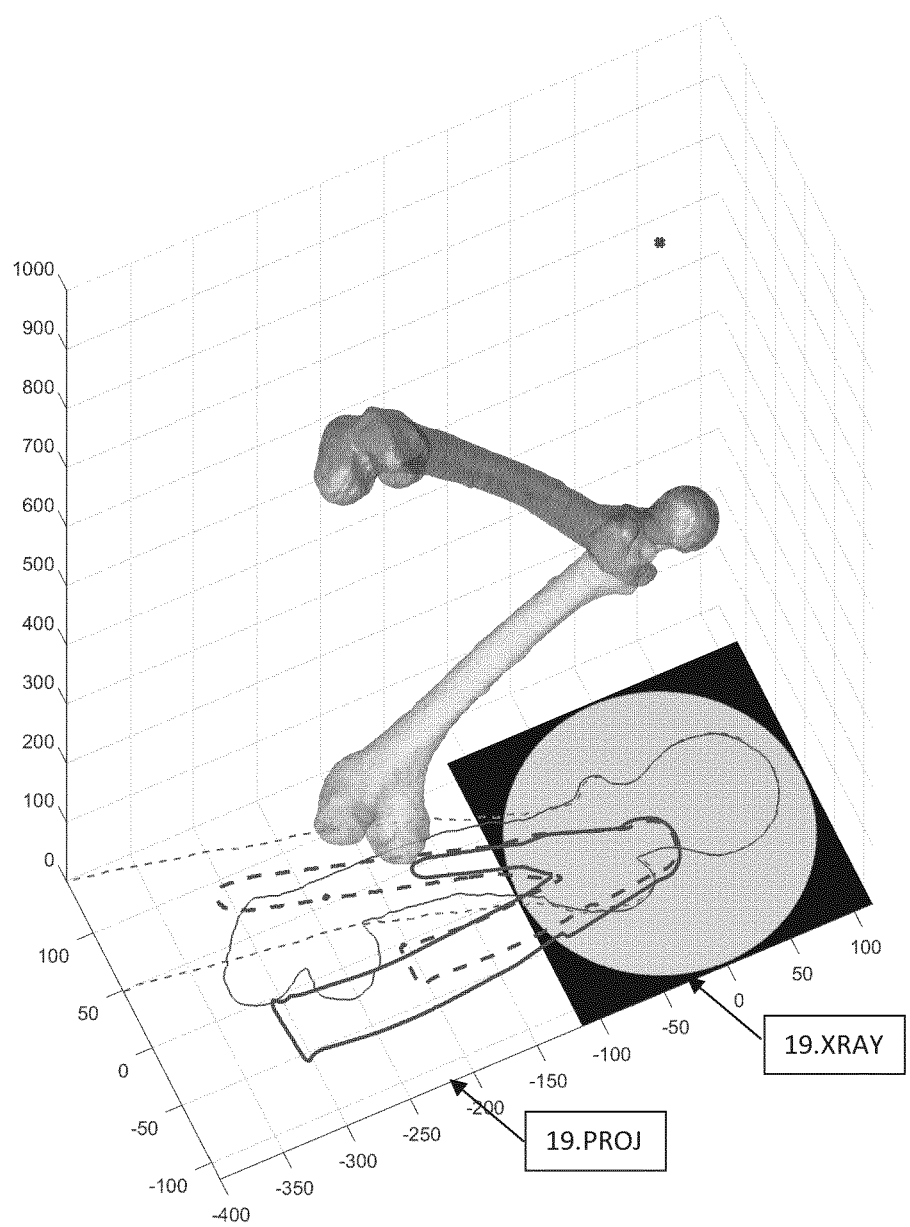
FIG. 19 illustrates the effect of receiving an LM image instead of an ML image in the projection plane.

Since in a typical ML image the nail has a lower distance to the image plane than the aiming device, these assumptions no longer hold when switching from ML to LM with an additional mirroring. FIG. 19 depicts the outlines of aiming device and nail in the projection plane (denoted 19.PROJ) for an ML image (thick solid line) and the corresponding mirrored LM image (thick dashed line). It can be seen that these outlines differ significantly. FIG. 19 also depicts the outlines of a femur for an ML view (thin solid line) and a mirrored LM view (thin dashed line) in the projection plane 19.PROJ. Within the field of view of the X-ray receiver (the rectangle denoted 19.XRAY), the outlines of the bones are almost identical. However, the outlines of aiming device and nail differ sufficiently within the rectangle 19.XRAY such that it is easily possible to distinguish between an ML image and a mirrored LM image.

Benefits of being Able to Determine the Imaging Direction Based on Different Approaches As mentioned before, the present invention as disclosed in Blau 917 allow a determination of the imaging direction based on independent approaches utilizing different information. This may be used (i) to cross-validate the results obtained by the different approaches and/or (ii) to enhance the precision of computing an imaging direction by appropriately fusing the results obtained by the different approaches. In the following, examples showing the benefits of this approach are shown.

Example 1: A critical question that may arise in the processing of a series of X-ray images is whether there has been a movement of an object relative to another object also depicted in the X-ray image, e.g., nail relative to anatomy. If there has been a movement, it may be necessary to compute it. A complicating factor is that, when an object moves in the X-ray projection image, it may be due only to a movement of the C-arm imaging device. The present invention allows differentiating between a movement of the C-arm imaging device and a movement of an object. In the following, it is explained how a movement of the nail relative to the patient can be detected. The present invention addresses this problem by determining the viewing direction onto anatomy (e.g., as disclosed in Blau 917) together with the position and orientation of the nail. Hence, it is possible to determine at which angle the C-arm views the nail, and at which angle it views the anatomy. Based on two subsequent X-ray images taken in AP direction, it is possible to detect whether the nail was rotated around its axis, even if there was a (slight) C-arm rotation between the images. Such detection is important because it may happen in the surgical procedure that when adjusting the entry depth of the nail, it may also inadvertently be rotated.

Example 2: An existing system requires that when attempting a 3D registration there be no movement of the implant relative to anatomy when switching between AP and ML views. Ignoring this requirement may result in an incorrect 3D registration. This example refers to the example for a potential processing workflow. In this processing workflow, the 3D angle between two viewing directions is computed based on two approaches (cf. Steps 3, 12, and 13), one based on anatomy (as disclosed in Blau 917) and one utilizing the implant assembly as a reference. If both calculations are considered correct (such determination may be made based on viewing direction, visibility of anatomy, image quality, etc.) yet differ more than a threshold, the system concludes that there has been a movement of the nail relative to the anatomy in between the acquisition of the two images, and it will thus inform the user. It may also be possible to automatically correct for a movement (cf. Example 1).

If a 3D registration procedure is successful, it may lead to higher accuracy in localization and 3D reconstruction. For instance, it may help resolve ambiguities that may exist when processing a single image only.

Example for a Potential Processing Workflow for a Distal Locking Procedure

Figure 20:
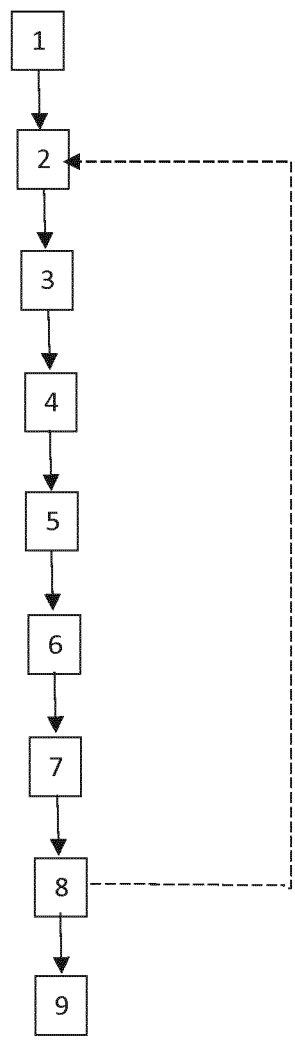
FIG. 20 shows an example for a possible workflow.

The flow-chart in FIG. 20 illustrates the principle of the steps performed in accordance with an embodiment of the disclosed invention. It will be understood that the steps described are major steps, wherein these major steps might be differentiated or divided into several sub-steps. Furthermore, there might be also sub-steps between these major steps. It will also be understood that only part of the whole method may constitute the invention, i.e. steps may be omitted.

This workflow refers to a long antegrade femoral nail with locking procedure from the lateral side. A similar procedure may be employed for retrograde nails, tibia, or humerus, and/or locking from other sides, e.g., the anterior side.
1. The long aiming device needs to be assembled and mounted. The locking sleeve assembly is inserted.
2. A lateral X-ray image of the distal femur is acquired. In the state-of-the-art, a specific viewing angle is required for this step. The present invention does not require a specific imaging direction, as long as the long aiming device is visible in the X-ray.
3. The long aiming device is localized. If the C-arm is not positioned appropriately (e.g., sleeve is not sufficiently visible), the device may compute a necessary adjustment (since the system knows where the sleeve is localized relative to the long aiming device) and give appropriate instructions on how to achieve this adjustment (rotation and translation of C-arm).
4. The device determines the position and outline where the unbent nail would be expected in the X-ray projection image (taking into account the intercept theorem).
5. The actual position of the nail is determined by matching a virtual projection of the nail model to the appearance of the nail in the X-ray image. This match may take into account the following:
   a. Expected position and outline of unbent nail in the X-ray projection image
   b. Object characteristics of nail, in particular, possible bending in AP and ML direction, nail thickness and material, wobbling in connection between nail and aiming device. For example, a thick nail may bend less and may have negligible torsion.
   c. Image characteristics and X-ray attenuation, absorption, and deflection.

This allows the computation of the relative 3D position between the distal part of the nail and the long aiming device.
6. The 3D position of the axis of the targeted nail hole (which may have the shape of a cylinder) is determined relative to the axis of the sleeve (which is determined by position of long aiming device and sleeve). The device determines the distance of sleeve axis and nail axis. Depending on the type of long aiming device and which hole is targeted (this may be known a priori), the system computes how the long aiming device needs to be adjusted in order to compensate for this distance.
7. Long aiming device is adjusted.
8. Steps 2 to 7 are repeated until distance between hole and sleeve axes is sufficiently small.
9. The surgeon may now proceed with distal locking.

The distance of image detector to focal point may not be available in practice. It is shown in the examples below that the error introduced by the fact that the aiming device's imaging depth is only estimated, is sufficiently small, provided that the targeted hole is sufficiently close to the image center (which may be ensured by giving appropriate C-arm positioning instructions).

For the following example, the long aiming device is located at a distance of 180 mm from the nail (towards the focal point). Hence, in distal ML images, long aiming device and nail have a different distance from the image plane. Since the relative locations of long aiming device and nail are known, the nail contour can be projected correctly onto the image plane.

Figure 21:
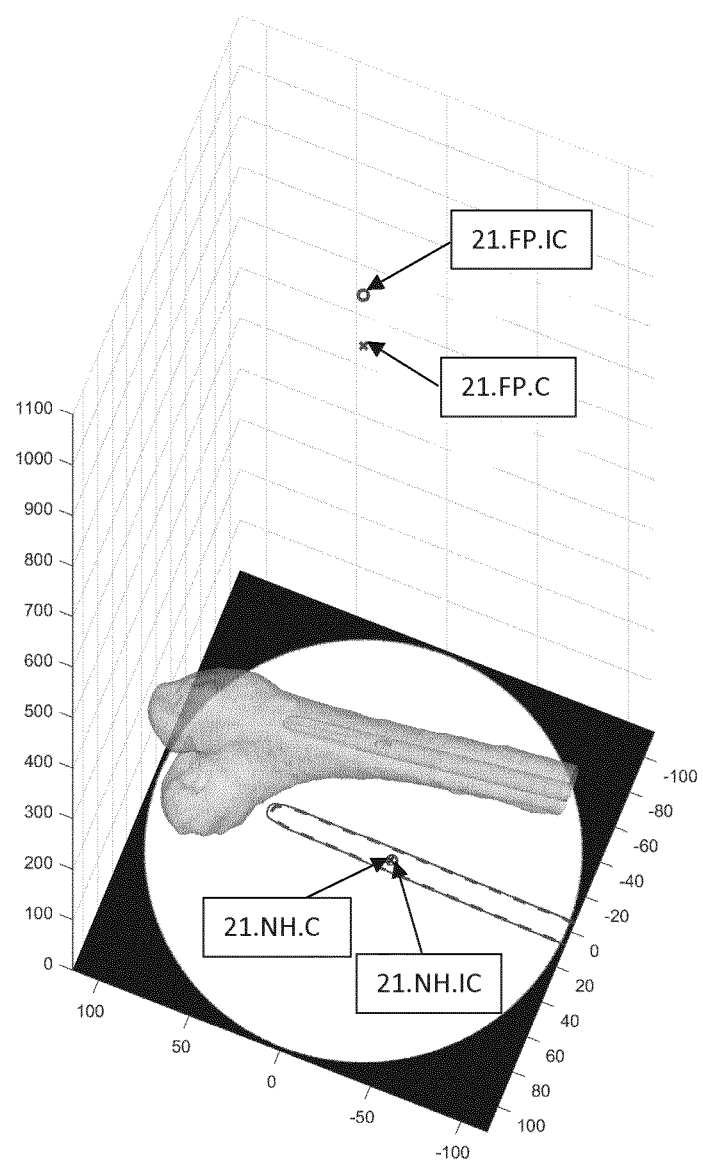
FIG. 21 shows the effect of using an incorrect focal point on distal locking support.

If the focal point is estimated incorrectly, for example 1100 mm instead of 1000 mm (which is a worst-case scenario), the error is small for points in the vicinity of the image center. This is shown in FIG. 21, where the correct focal point is denoted 21.FP.C, and the incorrect focal point is denoted 21.FP.IC. The corresponding nail outline in the 2D projection image is the solid line in the incorrect case, which is almost indistinguishable from the dashed line in the correct case, and the corresponding nail holes are denoted by 21.NH.C (correct nail hole indicated by the "x") and 21.NH.IC (incorrect nail hole indicated by the circle). For the given constellation, the nail hole has a height of 220 mm, and its 2D projection has a distance of 15 mm from the image center. The location of the incorrect nail hole deviates from the correct nail hole by only 0.65 mm, which is negligible for the purpose of distal locking.

Figure 22:
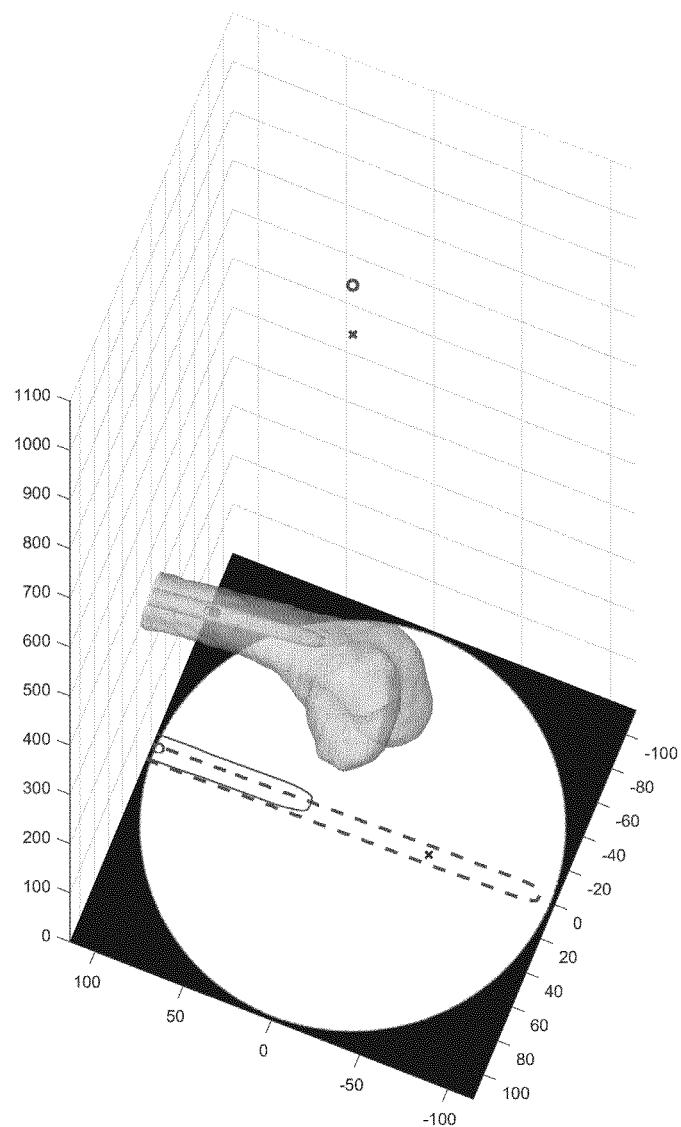
FIG. 22 shows the effect of receiving a PA image instead of an AP image on distal locking support.

It is also noted that exchanging the positions of X-ray source and receiver does not present a problem because this can be addressed as discussed in the section "Handling an exchange of the positions of X-ray source and receiver." If the C-arm is rotated by 180 degrees such that the focal point and the image plane exchange their position, the long aiming device will have a lower distance to the image plane than the nail implant. As FIG. 22 shows, the outline of the nail with rotated C-arm (denoted by the dashed line) will deviate extremely from the outline of the nail with unrotated C-arm (denoted by the solid line). Hence, the effect of exchanging positions of X-ray source and receiver is easy to detect.

Distal locking may also be performed free-hand, i.e. without the support of a long aiming device. It is assumed for the following exemplary method that the nail has a multiplicity of locking holes whose axes may or may not lie in the frontal plane.

After insertion of a nail into a long bone, the nail, for example a nail for a femur, is first fixated within the bone at the insertion end. The fixation or locking of the nail at the other end mostly requires moving the C-arm of an imaging system to that end.

As described above, the invention provides a system that is able to determine objects as well as geometrical aspects thereof on the basis of X-ray images, wherein such objects may be a bone or an implant but also a tool like a scalpel, an aiming device or a drill.

1. In general, an incision through the skin will be made, e.g. by means of a scalpel, followed by drilling a bore into the bone. A locking screw can be properly inserted if the bore is aligned with a through bore in the nail. An appropriate position for the incision as well as the position and orientation of the drill can be found on the basis of information determined and calculated by processing of X-ray image data. Basically, it is possible to determine the required position and orientation for the object like the scalpel or the drill on the basis of an oblique lateral image. For this, the system may utilize additional information from a firstly acquired AP (anterior to posterior) image.

2. The surgeon may move the C-arm into a distal AP position and may acquire an X-ray image. If the C-arm's orientation is insufficient for system guidance, the system may instruct the surgeon how to adjust the C-arm's orientation. This may be achieved based on the viewing direction (which may be determined based on the X-ray image, e.g., as disclosed in Blau 917) onto the implant or anatomy.

3. The system may detect in the AP image the nail and the distal locking holes and may measure the distance from the nail axis to the lateral surface of the bone perpendicular to the nail axis or measure the distance from at least one of the holes to the lateral surface of the bone. It may also measure the distance from at least one of the holes to the skin surface. The system may also assist the surgeon in applying a marking to the skin at the level of each hole. In order to determine the needed length of a (e.g. bi-cortical) locking screw for a later step, the system may also measure the distance between the nail axis and medial bone surface, accordingly. Such measured distances may be used as a priori information when processing subsequent lateral images (true ML and/or oblique lateral images).

4. Alternatively or additionally, a further improvement may be achieved by a determination of an insertion axis for the locking screw.

The surgeon may move the C-arm into a distal true ML position and acquire an X-ray image. For example, the C-arm may be in a true lateral position if a distal locking hole appears as a perfect circle in an acquired X-ray projection image. If needed, the system may support the surgeon by providing precise instructions for any required C-arm adjustment. The needed position and orientation of C-arm may thus be achieved more efficiently and with fewer iterations.

5. Additionally or alternatively, the system may match a statistical 3D model of the bone and thus determine the 3D position of the nail relative to the 3D position of the bone, thus enabling a determination of the needed locking screw length in 3D. Also, the information acquired from a true ML image may be used as a priori information when processing subsequent oblique lateral images.

6. The system assists the surgeon in making a first incision for an insertion of the distal locking screw. As soon as a scalpel is placed at an assumed location for the incision, an X-ray is acquired (true or oblique lateral), and the system then instructs the surgeon how the adjust the position and orientation of the scalpel so as to start an insertion of the locking screw at an appropriate entry point. Then, the surgeon makes the incision.

An alternative procedure, described in the following, differentiates between a hole whose axis lies in the frontal plane and a whole whose axis does not lie in the frontal plane. If the hole axis lies in the frontal plane, the system assists the surgeon in moving the C-arm such that the central X-ray beam is parallel to the frontal plane. In the more general case (if the hole axis does not lie in the frontal plane), the system assists the surgeon in moving the C-arm such that the 2D projection of the hole has maximum diameter in the direction perpendicular to the nail axis.

This may be achieved based on the viewing direction (which may be determined based on the X-ray image, e.g., as disclosed in Blau 917) onto the implant or anatomy. For each locking hole, the surgeon makes the incision such that the scalpel lies on the marking applied in Step 3 above and at the same time matches the nail axis in the X-ray projection.

7. With the C-arm in a lateral position, the surgeon positions a drill (with or without sleeve) such that the drill's tip in an acquired X-ray image is located on the central axis of the locking hole, i.e. at the center of the distal locking hole when seen along that axis. The system may detect the drill's tip and the locking hole, may calculate their relative position and may provide guidance on repositioning of the drill, if required. A further x-ray image to verify the position may be acquired.

8. Without changing the position of the drill's tip, the surgeon adjusts the drill's orientation. For example, the drill's axis may be roughly parallel to the true lateral X-ray imaging direction. With the C-arm in an oblique lateral position, the system may verify the drilling direction by utilizing the information of the drill tip's distance to the locking hole (as it is positioned on the bone surface) and the information that the drill's tip lies on the correct locking trajectory.

9. The system may use the information from earlier images to more accurately calculate the position and orientation of the drill (drill sleeve). E.g., a first image may be acquired when tip of instrument is on bone and the system uses the information of the distance between lateral bone surface and nail axis to calculate relative position and orientation of instrument and implant. A second image may be acquired during drilling in bone and the system may use the information of the relative position and orientation of the previous image (like the trajectory) instead of utilizing the distance between bone surface and implant.

Support and Evaluation of Reduction

A sufficiently correct reduction of a fracture is essential for a satisfactory clinical outcome in any osteosynthesis procedure. Typically, fractures heal satisfactorily only if the reduction was correctly performed. Reductions of long bones in particular are often difficult to evaluate during surgery, especially concerning a correct angle of anteversion. An incorrect angle of anteversion is often noticed only after completed surgery when the patient is able to stand up again. At this stage, an incorrect angle of anteversion causes major discomfort to the patient, even if the fracture itself healed properly. Indeed, an incorrect angle of anteversion is one of the major causes for revision surgery. Thus, a sufficiently correct angle of anteversion is essential for a satisfactory clinical outcome, especially for osteosynthesis of the femur and the tibia.

The prior art proposes different approaches to determine the angle of anteversion. In case of a femur and a cephalomedullary nail, one approach is to determine by hand whether the knee is pointing upwards to the ceiling of the operating room and to judge subjectively whether the screw, which should intersect the nail axis and the center of the femoral head, makes an angle of approximately 10 degrees with the floor of the operating room. Another approach is proposed by Blau et al. (patent application US 2015/0265361 A1) where two reference bodies with metallic markers, one in the distal region and one in the proximal region of the femur, and two proximal X-ray images and one distal X-ray image, all depicting the respective reference body, are used.

In the following, different methods to evaluate whether bone fragments are anatomically reduced are discussed. It is noted that these techniques do not require a determination of 3D positions or 3D orientations.

Figure 23:
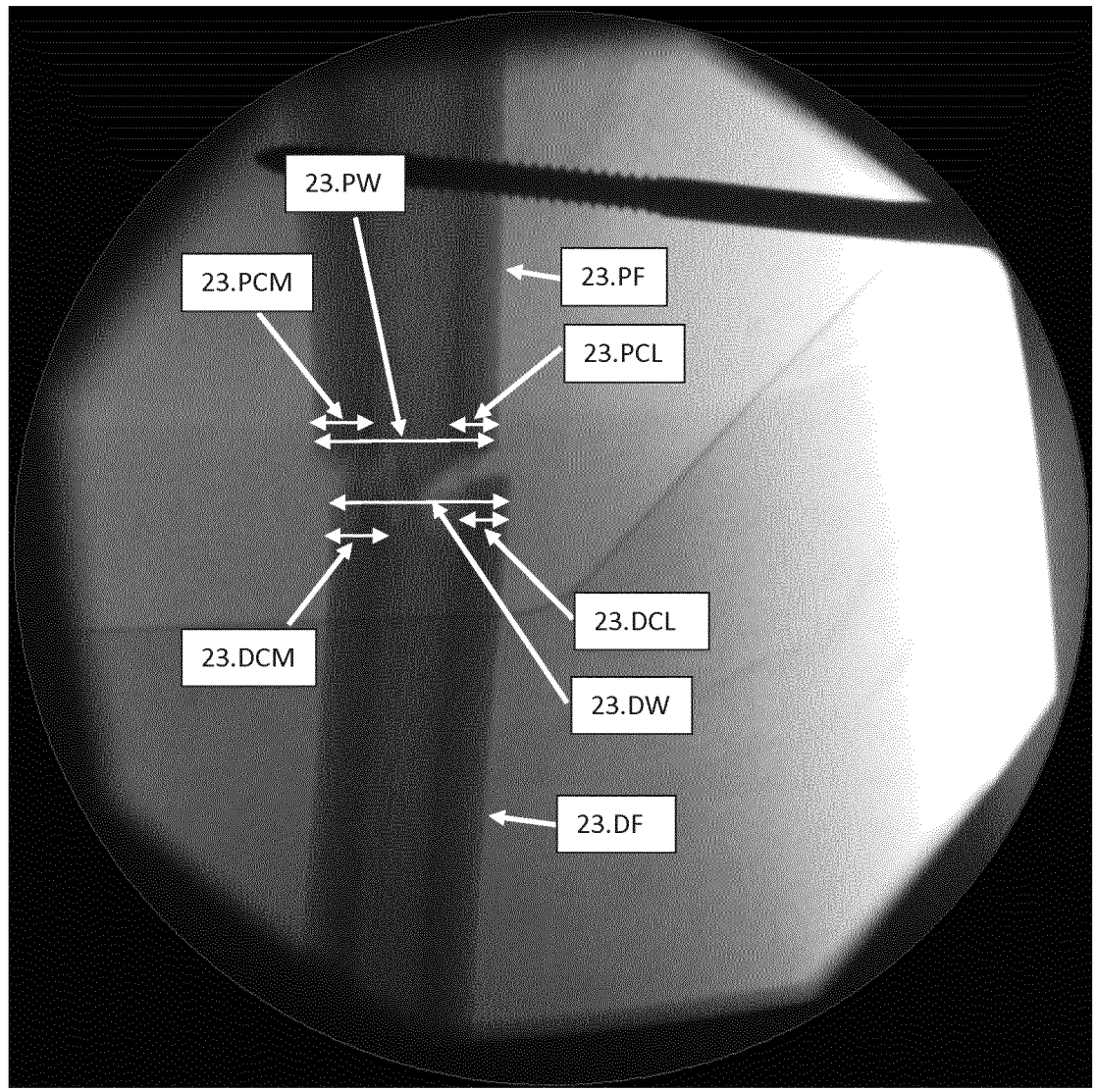
FIG. 23 shows a scenario for reduction evaluation.

Method A.:

One method is to measure the thickness of the bone fragments and the thickness of the cortexes as they appear in the X-ray image. This will be explained at the example of a broken femur shaft shown in FIG. 23. In this figure, the proximal part of the femur is denoted 23.PF, and the distal part is denoted 23.DF. In the X-ray image, the proximal femur appears to have a width of 23.PW next to the fracture line, and the distal part appears to have a width of 23.DW next to the fracture line. If these two widths differ, it may be concluded that the fragments are malrotated with respect to each other. Moreover, the thickness of the medial cortex of the proximal fragment next to the fracture line (denoted 23.PCM) must be sufficiently close to the thickness of the medial cortex of the distal fragment next to the fracture line (denoted 23.DCM). Analogously, the thickness of the lateral cortex of the proximal fragment next to the fracture line (denoted 23.PCL) must be sufficiently close to the thickness of the lateral cortex of the distal fragment next to the fracture line (denoted 23.DCL).

All three conditions must be met simultaneously for a correct reduction of the fracture. If at least one of these conditions is violated, this is normally caused by a rotation around the shaft axis, as the shaft of long bones is typically not perfectly round. The more the cross-section through the bone (perpendicular to the shaft) deviates from a disk, the more sensitive this method is to slight rotations around the shaft axis.

This method may be performed manually or automatically. Therefore, there is no need to calibrate images as all measurements are relative to each other and are performed in a similar imaging depth. A neural net may decide whether or not the above conditions for correct reduction are met.

Method B.:

Moreover, the fracture line is typically not straight and perpendicular to the shaft axis. Hence, if the fracture is not comminuted, an evaluation of the shape of the fracture line may supply critical information on a correct reduction, as the shape of the proximal fracture line must match the shape of the distal fracture line. This fracture line may be as disclosed in Blau 917. A neural net may decide whether or not the above conditions for correct reduction are met.

Method C.:

Another possibility to evaluate whether or not a reduction is anatomically correct is the visibility of other typical landmarks of the bone fragments. For the example of a broken femur shaft, the lesser trochanter is a particularly suitable landmark to evaluate the rotational alignment of the proximal fragment of a femur. This may be based on the degree of visibility of the lesser trochanter in an AP image, as it vanishes if the bone is rotated around the shaft axis. For the distal fragment, in a true AP image, the patella would be centered between the condyles.

In an AP imaging direction, the C-arm may easily be moved, parallel to the shaft axis, from a distal to a proximal location or vice versa without rotating the C-arm. For the example of a broken femur shaft, after acquiring a true AP image of the knee, the C-arm may be moved to the hip. If the proximal femur then also appears in a typical position for an AP imaging direction (e.g., based on the visibility of the lesser trochanter), it may be concluded that the rotational alignment and thus the anatomical reduction of the femur shaft fracture has been correctly achieved.

Combining the Methods

By combining the methods described in A. to C. above, the reduction may be better evaluated. An algorithm may fuse the information obtained from these different methods and provide an overall evaluation of the quality of reduction. This may involve a weighting of the different methods, where different weighting schemes are possible. For instance, one method may always be weighted more highly than other methods, e.g., method A may be weighted more highly than method C because C is based on a typical appearance of the average anatomy and A is patient-specific. The weighting may also be based on a confidence value that could be calculated by the system for the result of each method. Such a weighting may be based on image quality (poor quality means lower confidence value) or fracture type (less clear fracture line means lower confidence value).

The fusion of information as described in the previous paragraph may be performed by a neural net trained on a sufficiently big sample size of correctly reduced and not correctly reduced fractures. After an appropriate training this DNN could be able to classify whether a reduction is correct or incorrect and could provide that information to a user.

In the following, exemplary embodiments related to the invention are listed:

Embodiment 1. A system for determining a 3D representation and localization of an object in an X-ray projection image with respect to a coordinate system, the system comprising a processing unit configured to execute a computer program product including sets of instructions causing the system
  to receive an X-ray projection image,
    to classify an object in the X-ray projection image,
    to receive a model of the classified object,
    to determine a 3D representation of the classified object, and
    to localize the classified object with respect to the coordinate system, by applying the model to match the classified object in the X-ray image.

Embodiment 2. A system for determining a 3D representation and localization of a first object in an X-ray projection image with respect to a second object, the system comprising a processing unit configured to execute a computer program product including sets of instructions causing the system to receive an X-ray projection image,
to classify a first object in the X-ray projection image,
to receive a first model of the first object,
to determine at least a partial representation of the first object and a localization of the first object, by applying the first model to match the first object in the X-ray image,
to classify a second object in the X-ray projection image,
to receive a second model of the second object,
to determine at least a partial representation of the second object and a localization of the second object, by applying the second model to match the second object in the X-ray projection image, and
to determine a spatial relation of the classified objects.

In the following, it is referred to the one model of Embodiment 1 or to one of the first and second models of embodiment 2, when mentioning "the model". The same counts for "the object".

Embodiment 3. The system of embodiment 1 or 2, wherein the match of the model with the classified object takes into account image characteristics of the X-ray projection image, wherein the image characteristics depend on at least one imaging parameter and include at least one out of the group consisting of a pillow effect, a curvature, noise, distortion, and the X-ray imaging generation method.

Embodiment 4. The system of any one of embodiments 1 to 3, where the match of the model with the classified object takes into account the effects of at least one out of the group of X-ray attenuation, absorption, and deflection.

Embodiment 5. The system of any one of embodiments 1 to 4, wherein at least part of the outline of the classified object is detected in the X-ray projection image.

Embodiment 6. The system of any one of embodiments 1 to 5, wherein the system is further caused to localize a further object, wherein that object may even be not visible or only partially visible in the X-ray image.

Embodiment 7. The system of any one of embodiments 1 to 6, wherein the computer program further includes sets of instructions causing the system to transfer geometrical aspects from the model to the object.

Embodiment 8. The system of embodiment 7, wherein the computer program further includes sets of instructions causing the system to display the X-ray projection image together with those geometrical aspects.

Embodiment 9. The system of embodiment 7, wherein the geometrical aspects include sizes, wherein the sizes define a scale suitable for measuring dimensions in the X-ray projection image.

Embodiment 10. The system of any one of embodiments 3 to 9, wherein at least one of the imaging characteristics is determined by using an object of known shape for calibration, by automatic detection of imaging direction, based on information from a database.

Embodiment 11. The system of any one of embodiments 5 to 10, wherein at least one of the steps of classifying an object in the X-ray projection image, detecting the outline of the classified object in the X-ray projection image, determining a 3D representation of the classified object, localization of the classified object, determining image characteristics, determining object characteristics, determining X-ray attenuation, absorption, deflection, is assisted by user input.

Embodiment 12. The system of any one of embodiments 5 to 11, wherein at least one of the steps of classifying an object in the X-ray projection image, detecting the outline of the classified object in the X-ray projection image, determining a 3D representation of the classified object, localization of the classified object, determining image characteristics, determining object characteristics, determining X-ray attenuation, absorption, deflection, is performed automatically.

Embodiment 13. The system of embodiment 12, wherein at least one of the steps of classifying an object in the X-ray projection image, detecting the outline of the classified object in the X-ray projection image, determining a 3D representation of the classified object, localization of the classified object, determining image characteristics, determining object characteristics, determining X-ray attenuation, absorption, deflection, is performed by a neural net.

Embodiment 14. The system of any one of embodiments 1 to 13, wherein the matching of the object in the X-ray projection image with the model includes an adaptation of image characteristics of the X-ray projection image to image characteristics of a virtual projection of the model and/or an adaptation of image characteristics of the virtual projection of the model to image characteristics of the X-ray projection image.

Embodiment 15. The system of any one of embodiments 1 to 14, wherein the matching of the object in the X-ray projection image takes into account object characteristics, which include at least one out of the group of wobbling of mechanical interfaces, material and/or bending of implants and tools, bone fractures.

Embodiment 16. The system of any one of embodiments 1 to 15, wherein the model is a statistical shape or appearance model.

Embodiment 17. The system of any one of embodiments 1 to 16, wherein an imaging direction of the X-ray projection image is inclined relative to an axis of the object.

Embodiment 18. The system of any one of embodiments 1 to 17, wherein the computer program further includes sets of instructions causing the system to determine the imaging direction of the X-ray projection image.

Embodiment 19. The system of any one of embodiments 1 to 18, wherein the computer program further includes sets of instructions causing the system to receive information representing a target localization of the object relative to a coordinate system and/or to another object, and to determine a deviation of a determined localization of the classified object from the target localization.

Embodiment 20. The system of any one of embodiments 1 to 19, wherein the computer program further includes sets of instructions causing the system to determine at least one geometrical aspect of the object and to determine a relation of the geometrical aspect relative to a coordinate system and/or relative to a geometrical aspect of another object.

Embodiment 21. The system of any one of embodiments 1 to 20, wherein the computer program further includes sets of instructions causing the system to receive a further X-ray projection image of the same object, and to determine a change of the spatial relation of the object to a coordinate system and/or to another object, based on a comparison of the spatial relation determined based on a first X-ray image with the spatial relation determined based on the further X-ray image.

Embodiment 22. The system of any one of embodiments 1 to 21, wherein the computer program further includes sets of instructions causing the system to receive at least one further X-ray projection image of the same object, wherein the imaging parameters and/or imaging direction of the X-ray projection images differ from each other, and to determine three-dimensional aspects of the object by combining information from the plurality of projection images.

Embodiment 23. The system of any one of embodiments 1 to 22, wherein the computer program further includes sets of instructions causing the system to receive at least one further X-ray projection image depicting the same object from a different imaging direction, wherein the 3D representation of the object is used to register the images.

Embodiment 24. The system of embodiment 23, wherein the registration of the images is used to determine a 3D representation and localization of at least one further object depicted at least partially in all of those X-ray images.

Embodiment 25. The system of any one of embodiments 1 to 24, wherein the match of a classified object is based on the fact that this object's 3D position is sufficiently close to an expected 3D position.

Embodiment 26. The system of any one of embodiments 1 to 25, wherein the match of a classified object is based on the fact that this object's 3D orientation is sufficiently close to an expected 3D orientation.

Embodiment 27. The system of any one of embodiments 1 to 26, wherein an exchange of the roles of X-ray source and X-ray receiver can be detected.

Embodiment 28. The system of any one of embodiments 1 to 27, wherein the imaging depth is determined based on at least one sufficiently large object in at least one of the received X-ray images.

Embodiment 29. The system of any one of embodiments 1 to 28, wherein the imaging depth is determined based on a prior calibration with a known object.

Embodiment 30. A method for determining a 3D representation and localization of an object in an X-ray projection image with respect to a coordinate system, the method comprising the steps of
 receiving an X-ray projection image,
 classifying an object in the X-ray projection image,
 receiving a model of the classified object,
 determining a 3D representation of the classified object and localizing the classified object with respect to the coordinate system, by applying the model to match the classified object in the X-ray image.

Embodiment 31. The method of embodiment 30, wherein matching of the model with the classified object takes into account image characteristics of the X-ray projection image, wherein the image characteristics depend on at least one imaging parameter and include at least one out of the group consisting of a pillow effect, a curvature, noise, distortion, and the X-ray imaging generation method.

Embodiment 32. The method of any one of embodiments 30 or 31, wherein matching of the model with the classified object takes into account the effects of at least one out of the group of X-ray attenuation, absorption, and deflection.

Embodiment 33. The method of any one of embodiments 30 to 32, further including the step of detecting at least part of the outline of the classified object in the X-ray projection image.

Embodiment 34. The method of any one of embodiments 30 to 33, further including the step of localizing a further object that is not visible or only partially visible in the X-ray image.

Embodiment 35. The method of any one of embodiments 30 to 34, further including the step of transferring geometrical aspects from the model to the object.

Embodiment 36. The method of embodiment 35, further including the step of defining a scale based on the geometrical aspects, for measuring dimensions in the X-ray projection image.

Embodiment 37. The method of any one of embodiments 30 to 36, wherein matching of the object in the X-ray projection image with the model includes an adaptation of image characteristics of the X-ray projection image to image characteristics of a virtual projection of the model and/or an adaptation of image characteristics of the virtual projection of the model to image characteristics of the X-ray projection image.

Embodiment 38. The method of any one of embodiments 30 to 37, wherein matching of the object in the X-ray projection image with the model takes into account object characteristics, which include at least one out of the group of wobbling of mechanical interfaces, material and/or bending of implants and tools, bone fractures.

Embodiment 39. The method of any of embodiments 30 to 38, further comprising the steps of receiving a further X-ray image and registering the X-ray images, taking into account a movement of the X-ray imaging device between an acquisition of the received first and second X-ray images.

Embodiment 40. The method of embodiment 39, wherein an amount of the movement of the X-ray imaging device is measured by sensors at the X-ray imaging device.

Embodiment 41. The method of any one of embodiments 30 to 40, further comprising the steps of receiving a further X-ray image and registering the X-ray images taking into account the geometry of a model, with the model having portions respectively extending into one of the X-ray images.

Embodiment 42. The method of any one of embodiments 30 to 41, further comprising the steps of receiving a further X-ray image, classifying one further object in each received X-ray image, wherein different portions of that object extend into the received X-ray images, respectively, and registering the X-ray images based on a known geometry of that object.

While at least one exemplary embodiment has been presented in the foregoing detailed description, it should be appreciated that a vast number of variations exist. It should also be appreciated that the exemplary embodiment or exemplary embodiments are only examples and are not intended as exclusive embodiments or to limit the scope, applicability, or configuration of the invention in any way. Rather, the foregoing detailed description will provide those skilled in the art with a convenient road map for implementing an exemplary embodiment, it being understood that various changes may be made in the function and arrangement of elements described in an exemplary embodiment without departing from the scope of the invention as set forth in the appended claims and their legal equivalents.

The invention claimed is:
1. A method comprising:
 receiving an X-ray projection image;
 classifying a first object in the X-ray projection image;
 receiving a first model of the first object;
 determining at least a partial first representation of the first object and a first localization of the first object, by applying the first model to match the first object in the X-ray image;
 classifying a second object in the X-ray projection image;
 receiving a second model of the second object;
 determining at least a partial second representation of the second object and a second localization of the second object, by applying the second model to match the second object in the X-ray projection image;
 determining a spatial relation of the first and second objects without determining an imaging depth thereof, wherein determining of the spatial relation of the first and second objects comprises moving the first model relative to the second model from the first localization along a vector corresponding to an imaging direction of the X-ray projection image for achieving a point of contact between the first and second models.

2. The method of claim 1, wherein the X-ray projection image comprises an image characteristic from a group including a pillow effect, a curvature, noise, distortion or a combination thereof, the method further comprising accounting for the image characteristic when matching at least one of the models with the respective object.

3. The method of claim 1, wherein at least one of the objects in the X-ray projection image comprises an object characteristic from a group including wobbling of mechanical interfaces, bending of implants, bending of tools, bone fractures, or a combination thereof, the method further comprising accounting for the object characteristic when matching at least one of the object with the respective model.

4. The method of claim 1, further comprising determining a 3D representation of at least one of the classified objects.

5. The method claim 1, further comprising:
receiving information related to an expected 3D characteristic from a group including an expected 3D position, an expected 3D orientation, or a combination thereof for at least one of the objects in the X-ray projection image; and
accounting for the expected 3D characteristic when matching at least one object with the respective model.

6. The method of claim 1, further comprising transferring geometrical aspects from at least one model to the respective object.

7. The method of claim 6, further comprising defining a scale based on the geometrical aspects for measuring dimensions relative to a coordinate system.

8. The method of claim 1, wherein the X-ray projection image comprises an X-ray characteristic from a group including X-ray attenuation, absorption, deflection, or a combination thereof, the method further comprising adjusting a virtual projection of at least one of the first and second models to account for the X-ray characteristic.

9. The method of claim 1, further comprising determining an imaging direction from an X-ray source to an X-ray receiver, and adjusting spatial relation of the first and second objects based on the imaging direction.

10. A system for determining an arrangement of objects relative to each other in an X-ray projection image, the system comprising a processing unit configured to execute a computer program product including sets of instructions causing the system to perform the following method:
receiving an X-ray projection image from an imaging device;
classifying a first object in the X-ray projection image;
receiving a first model of the first object;
determining at least a partial first representation of the first object and a first localization of the first object, by applying the first model to match the first object in the X-ray image;
classifying a second object in the X-ray projection image;
receiving a second model of the second object;
determining at least a partial second representation of the second object and a second localization of the second object, by applying the second model to match the second object in the X-ray projection image; and
determining a spatial relation of the first and second objects without determining an imaging depth thereof, wherein determining of the spatial relation of the first and second objects comprises moving the first model relative to the second model from the first localization along a vector corresponding to an imaging direction of the X-ray projection image for achieving a point of contact between the first and second models.

11. The system of claim 10, further comprising an X-ray imaging device.

12. The system of claim 10, further comprising a database.

13. A non-transitory computer readable medium comprising processor-executable instructions for reading data from a processor in communication with an X-ray imaging device, the processor-executable instructions when executed on the processor in a device configure the device to:
receive an X-ray projection image;
classify a first object in the X-ray projection image;
receive a first model of the first object;
determine at least a partial first representation of the first object and a first localization of the first object, by applying the first model to match the first object in the X-ray image;
classify a second object in the X-ray projection image;
receive a second model of the second object;
determine at least a partial second representation of the second object and a second localization of the second object, by applying the second model to match the second object in the X-ray projection image; and
determine a spatial relation of the first and second objects without determining an imaging depth thereof, wherein determining of the spatial relation of the first and second objects comprises moving the first model relative to the second model from the first localization along a vector corresponding to an imaging direction of the X-ray projection image for achieving a point of contact between the first and second models.

* * * * *